United States Patent
Curatolo

(10) Patent No.: US 10,150,835 B2
(45) Date of Patent: Dec. 11, 2018

(54) DUAL CURABLE COMPOSITION

(71) Applicant: Benedict S. Curatolo, Valley View, OH (US)

(72) Inventor: Benedict S. Curatolo, Valley View, OH (US)

( * ) Notice: Subject to any disclaimer, the term of this patent is extended or adjusted under 35 U.S.C. 154(b) by 169 days.

(21) Appl. No.: 15/275,910

(22) Filed: Sep. 26, 2016

(65) Prior Publication Data
US 2017/0009010 A1 Jan. 12, 2017

Related U.S. Application Data

(63) Continuation of application No. 14/210,851, filed on Mar. 14, 2014.

(60) Provisional application No. 61/793,635, filed on Mar. 15, 2013.

(51) Int. Cl.

| | |
|---|---|
| *C08L 83/00* | (2006.01) |
| *C08G 63/78* | (2006.01) |
| *C08G 63/00* | (2006.01) |
| *C08L 63/00* | (2006.01) |
| *C09D 163/00* | (2006.01) |
| *C09J 163/00* | (2006.01) |
| *C09D 4/00* | (2006.01) |
| *C08G 59/00* | (2006.01) |
| *C08G 63/695* | (2006.01) |
| *C08G 77/54* | (2006.01) |
| *C08K 3/22* | (2006.01) |
| *C08K 3/32* | (2006.01) |
| *C08K 3/36* | (2006.01) |
| *C08K 5/375* | (2006.01) |
| *C09D 5/08* | (2006.01) |
| *C09D 167/00* | (2006.01) |
| *C09D 183/14* | (2006.01) |
| *C09J 167/00* | (2006.01) |
| *C09J 183/14* | (2006.01) |
| *C08F 230/08* | (2006.01) |
| *C08F 220/34* | (2006.01) |
| *C08F 222/10* | (2006.01) |

(52) U.S. Cl.
CPC ............ *C08G 63/78* (2013.01); *C08G 59/00* (2013.01); *C08G 63/00* (2013.01); *C08G 63/695* (2013.01); *C08G 77/54* (2013.01); *C08K 3/22* (2013.01); *C08K 3/32* (2013.01); *C08K 3/36* (2013.01); *C08K 5/375* (2013.01); *C08L 63/00* (2013.01); *C09D 4/00* (2013.01); *C09D 5/08* (2013.01); *C09D 163/00* (2013.01); *C09D 167/00* (2013.01); *C09D 183/14* (2013.01); *C09J 163/00* (2013.01); *C09J 167/00* (2013.01); *C09J 183/14* (2013.01); *C08F 220/34* (2013.01); *C08F 222/1006* (2013.01); *C08F 230/08* (2013.01); *C08G 2150/90* (2013.01); *C08K 2003/2241* (2013.01); *C08K 2003/321* (2013.01); *C08K 2201/019* (2013.01); *C09J 2205/114* (2013.01)

(58) Field of Classification Search
CPC ....... C08L 33/08; C08L 33/01; C08G 63/695; C08G 77/60; C08G 77/00
See application file for complete search history.

(56) References Cited

U.S. PATENT DOCUMENTS

| | | | |
|---|---|---|---|
| 4,697,026 | A | 9/1987 | Lee et al. |
| 5,260,350 | A | 11/1993 | Wright |
| 5,312,943 | A | 5/1994 | Gaglani |
| 5,374,483 | A | 12/1994 | Wright |
| 5,378,734 | A | 1/1995 | Inoue |
| 5,426,132 | A | 6/1995 | Gaglani |
| 5,552,485 | A | 9/1996 | Mitra et al. |
| 5,674,941 | A | 10/1997 | Cho et al. |
| 5,679,458 | A | 10/1997 | Cho et al. |
| 5,804,301 | A | 9/1998 | Curatolo |
| 5,888,649 | A | 3/1999 | Curatolo et al. |
| 6,686,008 | B1 | 2/2004 | Merlin et al. |
| 6,750,309 | B1 | 6/2004 | Chu et al. |
| 8,920,885 | B2 | 12/2014 | Deantoni et al. |
| 2008/0118659 | A1 | 5/2008 | Deantoni et al. |
| 2009/0076217 | A1* | 3/2009 | Gommans ............ C09D 183/04 524/588 |
| 2009/0269504 | A1 | 10/2009 | Liao |
| 2013/0245149 | A1 | 9/2013 | Geiser et al. |

FOREIGN PATENT DOCUMENTS

| | | | |
|---|---|---|---|
| EP | 0 620 255 A1 | 10/1994 | |
| EP | 0 666 290 A1 | 8/1995 | |

(Continued)

OTHER PUBLICATIONS

Great Britain 1311067.1—Search Report, dated Dec. 23, 2013.
PCT/US2014/027331—International Search Report, dated Jul. 22, 2014.
PCT/US2014/027331—International Written Opinion, dated Jul. 22, 2014.

*Primary Examiner* — Maragaret G Moore
(74) *Attorney, Agent, or Firm* — Curatolo Sidoti Co., LPA; Joseph G. Curatolo

(57) ABSTRACT

A dual curable composition is provided, comprising a compound represented by formula (I):

$$(\text{acrylate})_a\text{-(A)-(silane)}_b \qquad (\text{I})$$

in which a and b are identical or different and are each represented by an integer greater than or equal to 1; and wherein the dual curable composition is radiation curable and/or moisture curable. The moiety A comprises at least one of an aliphatic hydrocarbon, a cycloaliphatic hydrocarbon, an aryl moiety, an ether, an ester, an amide, a urethane, a urea, a hydroxyl group-containing organic moiety, an acrylic oligomer, an epoxy oligomer, a urethane oligomer, a polyester oligomer, or mixtures thereof, and the dual curable composition has a molecular weight greater than or equal to 300.

91 Claims, No Drawings

(56) References Cited

FOREIGN PATENT DOCUMENTS

| | | |
|---|---|---|
| JP | 2005281528 A | 10/2005 |
| WO | WO 01/66656 A2 | 9/2001 |
| WO | WO 2012/066520 A1 | 5/2012 |
| WO | WO 2013/028135 A1 | 2/2013 |

* cited by examiner

DUAL CURABLE COMPOSITION

The present application is a continuation of co-pending U.S. Ser. No. 14/210,851, filed Mar. 14, 2014, which claims the benefit of the filing date, under 35 U.S.C. § 119(e), of U.S. Provisional Application for Patent Ser. No. 61/793,635, filed Mar. 15, 2013, which applications are incorporated herein by reference.

Many curable compositions have disadvantages with regard to environmental and efficiency considerations. Many compositions include solvents and hazardous materials which cause difficulties in use, including extended time periods for evaporation and cure, and health considerations for applicators and individuals in the vicinity of applied and curing compositions. Many compositions have only one cure mechanism which can lead to poor efficiency due to extended time requirements for cure and limitations with regard to required conditions for effective cure. The need exists for a dual curable composition that can provide fast and efficient cure for a coating, sealant, adhesive, or composite resin, without a solvent or hazardous components. There is a particular need for a dual curable composition that can provide solvent-free, isocyanate-free, and chromium-free protection for industrial and aerospace substrates.

A dual curable composition is provided, comprising a compound represented by formula (I):

$$(\text{acrylate})_a\text{-}(A)\text{-}(\text{silane})_b \qquad (I)$$

in which a and b are identical or different and are each represented by an integer greater than or equal to 1; and
the moiety A comprises at least one of an aliphatic hydrocarbon, a cycloaliphatic hydrocarbon, an aryl moiety, an ether, an ester, an amide, a urethane, a urea, a hydroxyl group-containing organic moiety, an acrylic oligomer, an epoxy oligomer, a urethane oligomer, a polyester oligomer, or mixtures thereof;
wherein the dual curable composition has a molecular weight greater than or equal to 300; and
wherein the dual curable composition is radiation-curable and/or moisture curable.

By "radiation-curable" is meant curable by radiation energy such as electron beam radiation or ultraviolet (UV) radiation, including sunlight, and includes the term "photo-curable".

The dual curable composition comprises at least one acrylate moiety. Throughout this specification and claims, the term "acrylate" is used generally to include derivatives of acrylic acids as well as substituted acrylic acids such as methacrylic acid, ethacrylic acid, etc., unless clearly indicated otherwise. The term "acrylate" is therefore intended to include substituted as well as unsubstituted acrylates. The term "acrylate" is intended to include alkyl acrylates with the alkyl group having from 1 up to about 8 carbon atoms. In certain embodiments, the alkyl group of the alkyl acrylate has 1 carbon atom, and in those embodiments the term "acrylate" corresponds to a methacrylate moiety. Other substituents include hydroxyl, chlorine, bromine, and fluorine.

The dual curable composition comprises at least one silane moiety. Throughout this specification and claims, the term "silane" is used generally to include organofunctional alkoxysilanes with each alkoxy group independently having from 1 up to about 8 carbon atoms. In certain embodiments, the alkoxy group of the organofunctional alkoxysilane has 1 carbon atom, and in those embodiments the term "silane" corresponds to an organofunctional methoxysilane. In other embodiments, the alkoxy group of the organofunctional alkoxysilane has 2 carbon atoms, and in those embodiments the term "silane" corresponds to an organofunctional ethoxysilane. In certain embodiments, the organofunctional alkoxysilane moiety has one alkoxy group, and in those embodiments the term "silane" corresponds to an organofunctional alkoxysilane. In other embodiments, the organofunctional alkoxysilane moiety has two alkoxy groups, and in those embodiments the term "silane" corresponds to an organofunctional dialkoxysilane. In other embodiments, the organofunctional alkoxysilane moiety has three alkoxy groups, and in those embodiments the term "silane" corresponds to an organofunctional trialkoxysilane.

In certain embodiments, the dual curable composition has a molecular weight greater than or equal to 300 and less than or equal to 1,000,000. In other embodiments, the dual curable composition has a molecular weight between 300 and about 100,000. In other embodiments, the dual curable composition has a molecular weight between 300 and about 20,000. In other embodiments, the dual curable composition has a molecular weight between 300 and about 10,000. In some embodiments, the dual curable composition has a molecular weight greater than or equal to 500. In other embodiments, the dual curable composition has a molecular weight between 500 and about 5,000. In some embodiments, the dual curable composition has a molecular weight greater than or equal to 1,000. In other embodiments, the dual curable composition has a molecular weight between 1,000 and about 4,000. While not being bound by theory, a molecular weight less than 300 may result in performance disadvantages. The molecular weight is a number average molecular weight either determined by end group analysis, calculated based on the sum of the atomic weights of the component atoms of the molecule, or calculated by a formula based on gel permeation chromatography (GPC).

In certain embodiments, the dual curable composition comprises a compound represented by formula (II) and/or formula (III):

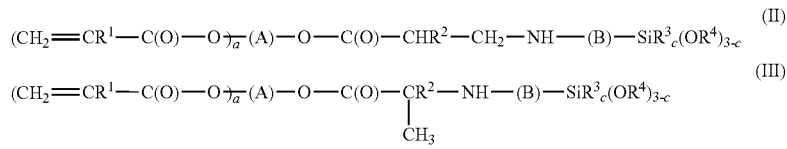

$$(CH_2{=}CR^1{-}C(O){-}O)_{\overline{a}}(A){-}O{-}C(O){-}CHR^2{-}CH_2{-}NH{-}(B){-}SiR^3_c(OR^4)_{3-c} \qquad (II)$$

$$(CH_2{=}CR^1{-}C(O){-}O)_{\overline{a}}(A){-}O{-}C(O){-}\underset{\underset{CH_3}{|}}{C}R^2{-}NH{-}(B){-}SiR^3_c(OR^4)_{3-c} \qquad (III)$$

in which
a is represented by an integer greater than or equal to 1;
c is an integer equal to 0, 1, or 2;
the moiety B comprises at least one of an aliphatic hydrocarbon, a cycloaliphatic hydrocarbon, an aryl moiety, an ether, an amide, or mixtures thereof;
wherein the moiety B has a molecular weight less than or equal to 500;
$R^1$ and $R^2$ are each independently H or an alkyl group having 1 to about 8 C (carbon) atoms; and $R^3$ and $R^4$ are each independently alkyl groups having 1 to about 8 C atoms. A is as defined above.

In other embodiments, the dual curable composition comprises a compound represented by formula (II), wherein a, c, A, B, $R^1$, $R^2$, $R^3$, and $R^4$ are defined above.

In certain embodiments, the dual curable composition comprises a compound represented by formula (IV) and/or formula (V):

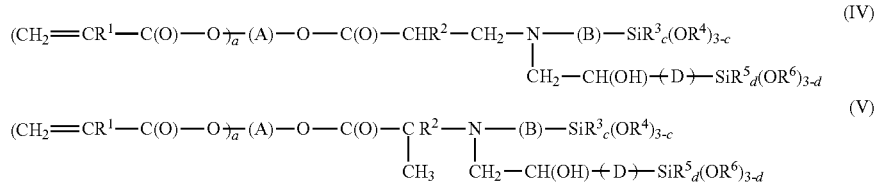

in which
d is an integer equal to 0, 1, or 2;
the moiety D comprises at least one of an aliphatic hydrocarbon, a cycloaliphatic hydrocarbon, an aryl moiety, an ether, or mixtures thereof;
wherein the moiety D has a molecular weight less than or equal to 500;
$R^5$, and $R^6$ are each independently alkyl groups having 1 to about 8 C atoms; and
a, c, A, B, $R^1$, $R^2$, $R^3$, and $R^4$ are defined above.

In other embodiments, the dual curable composition comprises a compound represented by formula (IV), wherein a, c, d, A, B, D, $R^1$, $R^2$, $R^3$, $R^4$, $R^5$, and $R^6$ are defined above.

In certain embodiments, the dual curable composition further comprises at least one additional component of a curable composition. In some embodiments the additional component comprises a reactive or curable component of a curable composition. In some embodiments the additional component comprises a non-reactive component of a curable composition.

In certain embodiments, the dual curable composition further comprises a silane. In certain embodiments, the dual curable composition further comprises at least one component comprising at least one silane moiety but not containing an acrylate moiety. In these embodiments, the overall mole ratio of silane moieties divided by the total of (acrylate moieties+silane moieties) is between 0.001 and 0.999. In other embodiments, the mole ratio is between 0.01 and 0.99. In other embodiments, the mole ratio is between 0.1 and 0.9. In all of these embodiments, the dual curable composition comprises at least one acrylate moiety and at least one silane moiety, but an overall formula representation for groups of components and molecules in these embodiments may represent each type of moiety as a non-integer, fraction, or decimal ratio, due to the different amounts of the moieties in the various components.

In certain embodiments, the dual curable composition further comprises an acrylate. In certain embodiments, the dual curable composition further comprises at least one component comprising at least one acrylate moiety but not containing a silane moiety. In these embodiments, the overall mole ratio of acrylate moieties divided by the total of (acrylate moieties+silane moieties) is between 0.001 and 0.999. In other embodiments, the mole ratio is between 0.01 and 0.99. In other embodiments, the mole ratio is between 0.1 and 0.9. In all of these embodiments, the dual curable composition comprises at least one acrylate moiety and at least one silane moiety, but an overall formula representation for groups of components and molecules in these embodiments may represent each type of moiety as a non-integer, fraction, or decimal ratio, due to the different amounts of the moieties in the various components.

The overall formula representation for an oligomer or polymer may likewise represent the amount of each type of moiety as a non-integer, fraction, or decimal ratio as a consequence of different molecules having different sizes in the oligomer or polymer composition, for the reasons discussed above.

In certain embodiments, the dual curable composition further comprises a reactive monomer. In certain embodiments, the reactive monomer comprises at least one of a monoacrylate monomer, diacrylate monomer, polyacrylate monomer, or mixtures thereof. In other embodiments, the reactive monomer comprises a vinyl monomer capable of polymerization with acrylate monomers. For purposes of illustration but not by way of limitation, in certain embodiments the reactive monomer comprises at least one of a vinyl ether, vinyl ester, vinyl carboxylic acid, vinyl carboxylic acid salt, vinyl amide, vinyl silane, allyl compound (generally of the types listed herein for vinyl compounds), unsaturated dicarboxylic acid, or mixtures thereof. In some embodiments, the reactive monomer comprises more than one type of reactive group. Each of the terms describing the reactive monomer types is used generally to also include derivatives thereof. The term "polyacrylate" is used generally to include triacrylates, tetraacrylates, pentaacrylates, hexaacrylates, and higher functionality acrylates. As explained previously, the term "acrylate" is intended to include unsubstituted as well as substituted alkyl acrylates and mixtures thereof, with the alkyl group having from 1 up to about 8 carbon atoms. Other substituents include hydroxyl, chlorine, bromine, and fluorine.

In certain embodiments, the monoacrylate monomer comprises at least one of butyl acrylate, ethylhexyl acrylate, 2-ethoxyethyl acrylate, cyclohexyl acrylate, 2-propylheptyl acrylate, lauryl acrylate, stearyl acrylate, behenyl acrylate, alkoxylated phenol acrylate, alkoxylated nonylphenol acrylate, nonylphenol acrylate, isobornyl acrylate, cyclic trimethylolpropane formal acrylate, dihydrodicyclopentadienyl acrylate, caprolactone acrylate, 2-phenoxyethyl acrylate, O-phenylphenoxyethyl acrylate, benzyl acrylate, hydroxyethyl acrylate, hydroxypropyl acrylate, hydroxybutyl acrylate, hydroxyethylcaprolactone acrylate, 2-hydroxy-3-phenoxypropyl acrylate, monomethoxy tripropylene glycol monoacrylate, monomethoxy neopentyl glycol propoxylate monoacrylate, tetrahydrofurfuryl acrylate, isooctyl acrylate, isodecyl acrylate, tridecyl acrylate, 2-(2-ethoxyethoxy) ethyl acrylate, cyclopentenyl oxyethyl acrylate, 9-anthracenyl methyl acrylate, 1-pyrenylmethyl acrylate, or mixtures thereof.

In certain embodiments, the diacrylate monomer comprises at least one of 1,3-butanediol diacrylate, 1,4-butanediol diacrylate, 1,6-hexanedioldiacrylate, 1,8-octanediol diacrylate, 1,10-decanediol diacrylate, polybutadiene diacrylate, ethylene glycol diacrylate, propylene glycol diacrylate, neopentyl glycol diacrylate, diethylene glycol diacrylate, triethylene glycol diacrylate, tetraethylene glycol diacrylate, polyethylene glycol diacrylate, dipropylene glycol diacrylate, tripropylene glycol diacrylate, tetrapropylene glycol diacrylate, polypropylene glycol diacrylate, glyceryl ethoxylate diacrylate, glyceryl propoxylate diacrylate, tricyclodecane dimethanol diacrylate, hydroxyl pivalic acid neopentyl glycol diacrylate, neopentylglycol ethoxylate diacrylate, neopentylglycol propoxylate diacrylate, monomethoxy trimethylolpropane ethoxylate diacrylate, monomethoxy trimethylolpropane propoxylate diacrylate, Bisphenol A ethoxylate diacrylate, and Bisphenol A propoxylate diacrylate, Fluorescein diacrylate, or mixtures thereof.

In certain embodiments, the polyacrylate monomer comprises at least one of trimethylolpropane triacrylate, glyceryl triacrylate, pentaerythritol triacrylate, pentaerythritoltetraacrylate, dipentaerythritol pentaacrylate, dipentaerythritol hexaacrylate, di-trimethylolpropane tetraacrylate, tris(2-hydroxyethyl)isocyanurate triacrylate, glyceryl ethoxylate triacrylate, glyceryl propoxylate triacrylate, trimethylolpropane ethoxylate triacrylate, trimethylolpropane propoxylate triacrylate, acrylated epoxy soya oil, acrylated epoxy linseed oil, pentaerythritol ethoxylate tetraacrylate, pentaerythritol propoxylate tetraacrylate, dipentaerythritol ethoxylate pentaacrylate, dipentaerythritol propoxylate pentaacrylate, di-trimethylolpropane ethoxylate tetraacrylate, di-trimethylolpropane propoxylate tetraacrylate, or mixtures thereof.

In certain embodiments, the vinyl ether comprises at least one of ethyl vinyl ether, butyl vinyl ether, hydroxy butyl vinyl ether, cyclohexyl vinyl ether, 1,4-cyclohexane dimethanol monovinyl ether, 2-ethylhexyl vinyl ether, octyl vinyl ether, decyl vinyl ether, dodecyl vinyl ether, octadecyl vinyl ether, cyclohexane dimethanol monovinyl ether, phenyl vinyl ether, 1,4-butanediol divinyl ether, 1,6-hexanediol divinyl ether, 1,4-cyclohexane dimethanol divinyl ether, diethylene glycol divinyl ether, triethylene glycol divinyl ether, tetraethylene glycol divinyl ether, dipropylene glycol divinyl ether, tripropylene glycol divinyl ether, tetrapropylene glycol divinyl ether, the propenyl ether of propylene carbonate, or mixtures thereof.

In certain embodiments, the vinyl ester comprises at least one of vinyl propionate, vinyl acetate, vinyl 2-ethyl hexanoate, or mixtures thereof.

In certain embodiments, the vinyl silane comprises at least one of vinyltrimethoxy silane, vinyltriethoxysilane, vinylmethyldimethoxysilane, vinyl-tris-(2-methoxyethoxy)silane, or mixtures thereof.

In certain embodiments, the allyl compound comprises at least one of allyl propoxylate, diallyl phthalate, tripropyleneglycol diallyl ether, pentaerythritol allyl ether, trimethylolpropane diallyl ether, trimethylolpropane monoallyl ether, triallyl cyanurate, triallyl isocyanurate, and hydroxy terminated ethyleneglycol bis[pentakis(glycidyl allyl ether)] ether, or mixtures thereof.

In certain embodiments, the reactive monomer that comprises more than one type of reactive group comprises at least one of allyl cinnamate (allyl 3-phenylacrylate), allyl acrylate, ethoxylated allyl acrylate, propoxylated allyl acrylate, di(propyleneglycol) allyl ether acrylate, corresponding allyl alkyl (C1 to about C8) acrylates as previously defined to be included by the term "acrylates", or mixtures thereof.

In certain embodiments, the dual curable composition further comprises an oligomer. In other embodiments, the dual curable composition further comprises a polymer. In certain embodiments, the oligomer comprises at least one of an aliphatic polyether urethane monoacrylate, aliphatic polyester urethane monoacrylate, aromatic polyether urethane monoacrylate, aromatic polyester urethane monoacrylate, polyester monoacrylate, polyether monoacrylate, epoxy monoacrylate, acrylated acrylic monoacrylate, aliphatic polyether urethane diacrylate, aliphatic polyester urethane diacrylate, aromatic polyether urethane diacrylate, aromatic polyester urethane diacrylate, polyester diacrylate, polyether diacrylate, epoxy diacrylate, acrylated acrylic diacrylate, polyacrylate monomer, aliphatic polyether urethane polyacrylate, aliphatic polyester urethane polyacrylate, aromatic polyether urethane polyacrylate, aromatic polyester urethane polyacrylate, polyester polyacrylate, polyether polyacrylate, epoxy polyacrylate, acrylated acrylic polyacrylate, or mixtures thereof. The term "polyacrylate" is used generally to include triacrylates, tetraacrylates, pentaacrylates, hexaacrylates, and higher functionality acrylates.

In certain embodiments, the dual curable composition further comprises a photoinitiator. In certain embodiments, the photoinitiator comprises at least one of a free radical photoinitiator, a cationic photoinitiator, or mixtures thereof.

In certain embodiments, the free radical photoinitiator comprises at least one of benzophenone, benzyldimethyl ketal, isopropylthioxanthone, bis(2,4,6-trimethybenzoyl) phenylphosphine oxide, bis(2,6-dimethoxybenzoyl)(2,4,4-trimethylpentyl)phosphine oxide, 2-hydroxy-2-methyl-1-phenyl-1-propanone, diphenyl(2,4,6-trimethybenzoyl) phosphine oxides, 1-hydroxycyclohexyl phenyl ketone, 2-benzyl-2-(dimethylamino)-1-[4-(4-morpholinyl)phenyl]-1-butanone, alpha,alpha-dimethoxy-(alpha-phenyl acetophenone, 2,2-diethoxyacetophenone, 2-methyl-1-[4-(methylthio)phenyl]-2-(4-morpholinyl)-1-propanone, 2-hydroxy-1-[4-(hydroxyethoxy)phenyl]-2-methyl-1-propanone, or mixtures thereof.

In certain embodiments, the dual curable composition further comprises a cationic photoinitiator. In some embodiments, the cationic photoinitiator comprises at least one of triarylsulfonium hexafluoroantimonate, triarylsulfonium hexafluorophosphate, diphenyl iodonium hexafluorophosphate, diphenyliodonium nitrate, triphenylsulfonium triflate, or mixtures thereof. In other embodiments, the cationic photoinitiator comprises at least one of diphenyl(4-phenylthio)phenylsulfonium hexafluoroantimonate, (thiodi-4,1-phenylene) bis(diphenylsulfonium) dihexafluoroantimonate, diphenyl(4-phenylthio)phenylsulfonium hexafluorophosphate, (thiodi-4,1-phenylene)bis(diphenylsulfonium) dihexafluoro phosphate, bis(p-tolyl)iodonium hexafluorophosphate, triarylsulfonium tetrakis [pentafluorophenyl] borate, (4-methylphenyl)[4-(2-methylpropyl)phenyl]-iodonium hexafluorophosphate, phenyl-p-octyloxyphenyl-iodonium hexafluorantimonate, diphenyliodonium perfluoro-1-butanesulfonate, 2-(4-methoxystyryl)-4,6-bis(trichloromethyl)-1,3,5-triazine, (4-phenoxyphenyl)diphenylsulfonium triflate, (4-phenylthiophenyl)diphenylsulfonium triflate, Tris(4-tert-butylphenyl)sulfonium triflate, methylbenzene reaction products with sulphur chloride hexafluorophosphate, or mixtures thereof. In certain embodiments, the cationic photoinitiator is optionally provided in a solution, such as, in one embodiment, a propylene carbonate solution.

In certain embodiments, the dual curable composition further comprises at least one of an epoxy monomer, oxetane monomer, or mixtures thereof. In certain embodiments, the dual curable composition further comprises a cycloaliphatic epoxy, (3-ethyl-3-oxetanyl)methyl acrylate, or mixtures thereof.

In certain embodiments, the dual curable composition further comprises at least one of a dispersant, pigment, filler, flow agent, leveling agent, wetting agent, surfactant, defoamer, rheology modifier, stabilizer, antioxidant, adhesion promoter, corrosion inhibitor, or mixtures thereof.

In certain embodiments, the dual curable composition further comprises a dispersant. In certain embodiments, the dispersant comprises a polymeric dispersant. In certain embodiments, the dispersant comprises a hyperdispersant.

In certain embodiments, the dual curable composition further comprises at least one of a pigment, filler, or mixtures thereof. In some embodiments, the dual curable composition further comprises at least one of titanium dioxide, colloidal silica, hydrophilic silica, hydrophobic amorphous fumed silica, amorphous precipitated silica, magnesium silicate, calcium carbonate, calcium silicate, aluminum silicate, aluminum oxide, barium sulfate, wollastonite, nepheline syenite, mica, carbon black, polymer powders, glass spheres, or mixtures thereof. In certain embodiments, the form of the filler or pigment comprises at least one of a powder, particle, plate, flake, sphere, hollow sphere, block, needle, fiber, or mixtures thereof. In certain embodiments, the size scale of the filler comprises at least one of macroscale, microscale, nanoscale, or mixtures thereof.

In certain embodiments, the dual curable composition further comprises at least one of a flow agent, leveling agent, wetting agent, surfactant, defoamer, or mixtures thereof. These may comprise at least one of a silicone, modified silicone, silicone acrylate, hydrocarbon solvent, fluorine-containing compound, non-silicone polymer or copolymer such as a copolyacrylate, or mixtures thereof.

In certain embodiments, the dual curable composition further comprises at least one of a stabilizer, an antioxidant, or mixtures thereof. In some embodiments, the dual curable composition further comprises at least one of a hydroxyphenylbenzotriazole, hydroxyphenyltriazine, oxalanilide, hindered amine light stabilizers (HALS), and acetylated hindered amine light stabilizers, or mixtures thereof. In certain embodiments, the dual curable composition further comprises at least one of 2-(2'-hydroxy-5'-methyl phenyl)-benzotriazole, 2-(3',5'-di-tert-butyl-2'-hydroxyphenyl)-5-chlorobenzotriazole, 2-(2'-hydroxy-3',5'-di-tert-amylphenyl)-benzotriazole, benzenepropanoic acid 3-(2H-benzotriazol-2-yl)-5-(1,1-dimethylethyl)-4-hydroxy-C7-9-branched alkyl esters, 2-(3',5'-bis(1-methyl-1-phenylethyl)-2'-hydroxyphenyl)benzotriazole, 2-[2-hydroxy-3-dimethyl benzylphenyl-5-(1,1,3,3-tetramethylbutyl)]-2H-benzotriazole, poly(oxy-1,2-ethane diyl)alpha[3-][3-(2H-benzotriazol-2-yl)-5-(1,1-dimethylethyl)-4-hydroxyphenyl]-1-oxopropyl]-omega-hydroxy and poly(oxy-1,2-ethanediyl)alpha-[3-][3-(2H-benzo triazol-2-yl)-5-(1,1-dimethylethyl)-4-hydroxyphenyl]-1-oxopropyl]-omega-[3-][3-(2H-benzotriazol-2-yl)-5-(1,1-dimethylethyl)-4-hydroxyphenyl]-1-oxopropoxy]-, 2-[4-[2-hydroxy-3-tridecyloxypropyl]oxy]-2-hydroxyphenyl]-4,6-bis(2,4-imethylphenyl)-1,3,5-triazine and 2-[4-[2-hydroxy-3-dodecyl oxypropyl]oxy]-2-hydroxyphenyl]-4,6-bis(2,4-dimethylphenyl)-1,3,5-triazine, bis(1,2,2,6,6-pentamethyl-4-piperidinyl)(3,5-di-tert-butyl-4-hydroxybenzyl) butylpropanedioate, bis(2,2,6,6-tetramethyl-4-piperidinyl) sebacate, tetrakis[methylene(3,5-di-tert-butyl-4-hydroxy-hydrocinnamate)] methane, thiodiethylene bis(3,5-di-tert-butyl-4-hydroxy-hydrocinnamate), octadecyl 3,5-di-tert-butyl-4-hydroxyhydro-cinnamate, bis(1,2,2,6,6-pentamethyl-4-piperidinyl)sebacate, methyl (1,2,2,6,6-pentamethyl-4-piperidinyl)sebacate, tris(2,4-di-tert-butylphenyl) phosphite, decanedioic acid bis(2,2,6,6-tetramethyl-4-piperidinyl) ester reaction products with 1,1-dimethyl-ethylhydroperoxide and octane, or mixtures thereof.

In certain embodiments, the dual curable composition further comprises an adhesion promoter. In certain embodiments, the adhesion promoter comprises an organic acid functional component. The term "organic acid-functional component" is used generally to include carbon based acid-functional components and derivatives thereof, and is intended to include carbon-containing components that additionally contain phosphorus based or sulfur based acidic groups. In certain embodiments, the organic acid functional component comprises at least one of an organic ester of phosphoric acid, an organic sulfonic acid, a sulfonium salt, or mixtures thereof. In certain embodiments, the organic acid functional component further comprises a reactive monomer functional group as defined above. In certain embodiments, the organic acid functional component comprises an acidic polymer.

In certain embodiments, the adhesion promoter comprises at least one of an acidic organophosphate acrylate, an acidic organophosphate alkyl (C1 to about C8) acrylate, or mixtures thereof.

In certain embodiments, the dual curable composition further comprises a corrosion inhibitor. In certain embodiments, the corrosion inhibitor comprises a chromate-free corrosion inhibitor. In certain embodiments, the chromate-free corrosion inhibitor comprises at least one of zinc phosphate, zinc phosphate tetrahydrate, zinc phosphosilicate, basic zinc phosphate silicate hydrate, calcium phosphate, calcium borosilicate, calcium phosphosilicate, strontium phosphosilicate, strontium zinc phosphosilicate, organically modified calcium zinc strontium phosphosilicate, zinc aluminium orthophosphate hydrate, organically modified basic zinc orthophosphate hydrate, basic zinc molybdenum orthophosphate hydrate, zinc aluminium polyphosphate hydrate, strontium aluminium polyphosphate hydrate, calcium aluminium polyphosphate silicate hydrate, organic modified zinc aluminium molybdenum orthophosphate hydrate, zinc calcium strontium aluminium orthophosphate silicate hydrate, calcium modified silica, zinc-5-nitroisophthalate, zinc salt of phthalic acid, or mixtures thereof.

In other embodiments, the chromate-free corrosion inhibitor comprises at least one of a Wayncor® or Hybricor™ corrosion inhibitor, or mixtures thereof, available from WPC Technologies, Inc., Milwaukee, Wis. In certain embodiments, the chromate-free corrosion inhibitor comprises at least one of Wayncor® 199, Wayncor® 214, Wayncor® 215, Wayncor® 227, Hybricor™ 204, Hybricor™ 204s, Hybricor™ 206, Hybricor™ 294, Hybricor™ 2000, or mixtures thereof.

In certain embodiments, the dual curable composition further comprises at least one of water, a hydroxyl-group containing organic compound, or mixtures thereof. In certain embodiments, the hydroxyl-group containing organic compound comprises at least one of a hydroxyl-group containing monomer, a hydroxyl-group containing oligomer, a hydroxyl-group containing polymer, or mixtures thereof. In certain embodiments, the hydroxyl-group containing organic compound comprises at least one of an epoxy oligomer, polyester oligomer, polyether oligomer, hydroxyl-terminated urethane oligomer, epoxy polymer, polyester polymer, polyether polymer, fluoroethylene/alkylvinylether copolymer, hydroxyl-terminated polyurethane, or mixtures thereof.

In certain embodiments, the dual curable composition comprises water for assistance in moisture curing, generally less than about 1 weight percent water. In other embodiments, the dual curable composition comprises less than 0.5 weight percent water. In other embodiments, the dual curable composition comprises less than 0.1 weight percent water.

In certain embodiments, the dual curable composition further comprises at least one of an organic titanate, a zirconate, a complex, and/or a carboxylate of lead, cobalt, iron, nickel, zinc, tin, or mixtures thereof. In some embodiments, the dual curable composition further comprises dibutyltin dilaurate.

In certain embodiments, the corrosion inhibitor comprises at least one of strontium chromate, zinc chromate, calcium chromate, or mixtures thereof, although the use of chromate materials can lead to health and environmental disadvantages.

In certain embodiments, the dual curable composition further comprises a solvent. In other embodiments, the dual curable composition is solvent-free.

A coating, sealant, adhesive, or composite resin is provided, comprising the dual curable composition comprising a compound represented by formula (I). In certain embodiments, a coating is provided, comprising the dual curable composition comprising a compound represented by formula (I). In other embodiments, a sealant is provided, comprising the dual curable composition comprising a compound represented by formula (I). In other embodiments, an adhesive is provided, comprising the dual curable composition comprising a compound represented by formula (I). In other embodiments, a composite resin is provided, comprising the dual curable composition comprising a compound represented by formula (I). Each of the coating, sealant, adhesive, or composite resin may comprise at least one additional component of a curable compound, as described above.

A two part coating, sealant, adhesive, or composite resin is provided, comprising Part A and Part B;

Part A comprising:

the dual curable composition comprising a compound represented by formula (I); and Part B comprising at least one of:

a corrosion inhibitor, an organic acid functional component, or mixtures thereof.

In certain embodiments, a two part coating, sealant, adhesive, or composite resin is provided;

Part A further comprising at least one of:

a photoinitiator, reactive monomer, defoamer, dispersant, pigment, stabilizer, or mixtures thereof; and Part B further comprising at least one of:

a dispersant, reactive monomer, defoamer, oligomer, adhesion promoter, surfactant, flow agent, or mixtures thereof.

For purposes of illustration but not by way of limitation, representative examples of components for Part A and Part B have been previously listed. While not being bound by theory, enhanced stability of Part A comprising the dual curable composition may be provided by the segregation of organic acid functional components and certain corrosion inhibitor components into Part B of the coating, sealant, adhesive, or composite resin.

A method of preparing the dual curable composition is provided, the method comprising:

reacting an acrylated component comprising at least two acrylate groups with an aminosilane to form a reaction product comprising at least one acrylate group and at least one silane group.

In certain embodiments, the acrylated component comprises at least one of a diacrylate monomer, aliphatic polyether urethane diacrylate, aliphatic polyester urethane diacrylate, aromatic polyether urethane diacrylate, aromatic polyester urethane diacrylate, polyester diacrylate, polyether diacrylate, epoxy diacrylate, acrylated acrylic diacrylate, polyacrylate monomer, aliphatic polyether urethane polyacrylate, aliphatic polyester urethane polyacrylate, aromatic polyether urethane polyacrylate, aromatic polyester urethane polyacrylate, polyester polyacrylate, polyether polyacrylate, epoxy polyacrylate, acrylated acrylic polyacrylate, or mixtures thereof.

In certain embodiments, the acrylated component comprises an acrylate grafted polymer. In certain embodiments, the acrylated component comprises at least one of an acrylated polyolefin, acrylated polytetrafluoroethylene, acrylated polyester, acrylated polyamide, or mixtures thereof.

In certain embodiments, the aminosilane comprises at least one of 3-amino propyltrimethoxysilane, 3-aminopropyltriethoxysilane, N-beta-(aminoethyl)-3-amino propyltrimethoxysilane, N-beta-(aminoethyl)-3-aminopropyl methyldimethoxy silane, N-beta-(aminoethyl)-3-aminopropyltriethoxysilane, delta-aminoneohexyl trimethoxysilane, delta-aminoneohexylmethyldimethoxysilane, delta-aminoneohexyl triethoxysilane, or mixtures thereof.

For purposes of illustration but not by way of limitation, in certain embodiments, the molar ratio of the acrylated component to the aminosilane (AC/AS) is in the range of about 1/0.5 to about 1/3. The calculated molecular weight of diacrylate monomer, polyacrylate monomer, and aminosilane based on the sum of the atomic weights of the component atoms of the molecules is used to determine the amount of moles in order to calculate this ratio, and the molecular weight of a repeating unit is used for diacrylate oligomers, polyacrylate oligomers, diacrylate polymers, and polyacrylate polymers. In certain embodiments, the (AC/AS) molar ratio is in the range of about 1/1 to about 1/2. In other embodiments, the (AC/AS) molar ratio is in the range of about 1/1 to about 1/1.5.

In certain embodiments, the method of preparing the dual curable composition further comprises:

contacting an additional component of a curable composition with the reaction product comprising at least one acrylate group and at least one silane group.

In certain embodiments, the method of preparing the dual curable composition further comprises:

reacting an epoxysilane with the reaction product comprising at least one acrylate group and at least one silane group to form a second reaction product comprising at least one acrylate group and at least two silane groups.

In certain embodiments, the epoxysilane comprises at least one of 3-glycidoxy propyltrimethoxysilane, 3-glycidoxypropyltriethoxysilane, 3-glycidoxypropylmethyl dimethoxysilane, 3-glycidoxypropylmethyldiethoxysilane, beta-(3,4-epoxycyclohexyl) ethyltrimethoxysilane, beta-(3,4-epoxycyclohexyl)ethyl triethoxysilane, or mixtures thereof.

For purposes of illustration but not by way of limitation, in certain embodiments, the molar ratio of the acrylated component to the aminosilane to the epoxysilane (AC/AS/ES) is in the range of about 1/0.5/0.5 to about 1/3/3. In certain embodiments, the (AC/AS/ES) molar ratio is in the range of about 1/1/1 to about 1/2/2. In other embodiments, the (AC/AS/ES) molar ratio is in the range of about 1/1/1 to about 1/1.5/1.5.

In certain embodiments, the method of preparing the dual curable composition method further comprises:

contacting an additional component of a curable composition with the second reaction product comprising at least one acrylate group and at least two silane groups.

In certain embodiments, a method of preparing the dual curable composition is provided, the method comprising:

reacting a hydroxyl-functional acrylated component comprising at least one hydroxyl group and one acrylate group with an isocyanatosilane to form a reaction product comprising at least one acrylate group and at least one silane group.

In certain embodiments, the hydroxyl-functional acrylated component comprises at least one of a hydroxymonoacrylate, hydroxydiacrylate, hydroxypolyacrylate, hydroxyl-functional aliphatic polyether urethane monoacrylate, hydroxyl-functional aliphatic polyester urethane monoacrylate, hydroxyl-functional aromatic polyether urethane monoacrylate, hydroxyl-functional aromatic polyester urethane monoacrylate, hydroxyl-functional polyester monoacrylate, hydroxyl-functional polyether monoacrylate, hydroxyl-functional epoxy monoacrylate, hydroxyl-functional acrylated acrylic monoacrylate, hydroxyl-functional aliphatic polyether urethane diacrylate, hydroxyl-functional aliphatic polyester urethane diacrylate, hydroxyl-functional aromatic polyether urethane diacrylate, hydroxyl-functional aromatic polyester urethane diacrylate, hydroxyl-functional polyester diacrylate, hydroxyl-functional polyether diacrylate, hydroxyl-functional epoxy diacrylate, hydroxyl-functional acrylated acrylic diacrylate, hydroxyl-functional aliphatic polyether urethane polyacrylate, hydroxyl-functional aliphatic polyester urethane polyacrylate, hydroxyl-functional aromatic polyether urethane polyacrylate, hydroxyl-functional aromatic polyester urethane polyacrylate, hydroxyl-functional polyester polyacrylate, hydroxyl-functional polyether polyacrylate, hydroxyl-functional epoxy polyacrylate, hydroxyl-functional acrylated acrylic polyacrylate, or mixtures thereof.

In certain embodiments, the hydroxyl-functional acrylated component comprises an acrylate grafted polymer with hydroxyl functionality. In some embodiments, the hydroxyl-functional acrylated component comprises an acrylate grafted polymer with at least one hydroxyl functional end group.

For purposes of illustration but not by way of limitation, in certain embodiments the hydroxyl-functional acrylated component comprises at least one of hydroxyethyl acrylate, hydroxypropyl acrylate, hydroxybutyl acrylate, hydroxyethylcaprolactone acrylate, 2-hydroxy-3-phenoxypropyl acrylate, pentaerythritol triacrylate, dipentaerythritol pentaacrylate, or mixtures thereof.

In certain embodiments, the isocyanatosilane comprises at least one of 3-isocyanatopropyltrimethoxysilane, isocyanatopropyltriethoxysilane, or mixtures thereof.

In certain embodiments, a method of preparing the dual curable composition is provided, the method comprising:

reacting an acrylated component comprising at least two acrylate groups with a mercaptosilane to form a reaction product comprising at least one acrylate group and at least one silane group.

In certain embodiments, the mercaptosilane comprises at least one of 3-mercaptopropyltrimethoxysilane, mercaptopropyltriethoxysilane, or mixtures thereof.

In certain embodiments, a method of preparing the dual curable composition is provided, the method comprising:

reacting a component comprising at least two isocyanate groups with a hydroxyacrylate and an aminosilane to form a reaction product comprising at least one acrylate group and at least one silane group.

The previously recited methods may further comprise contacting an additional component of a curable composition with the reaction product comprising at least one acrylate group and at least one silane group.

In certain embodiments, the component comprising at least two isocyanate groups comprises at least one of a diisocyanate monomer, diisocyanate oligomer, diisocyanate-terminated pre-polymer, diisocyanate-terminated polymer, polyisocyanate monomer, polyisocyanate oligomer, polyisocyanate-terminated pre-polymer, polyisocyanate-terminated polymer, or mixtures thereof. In certain embodiments, the diisocyanate-containing components at least one of a polyurethane or polyurea oligomer, pre-polymer, polymer, or mixtures thereof. The term "polyisocyanate" is used generally to include components with more than two isocyanate groups, including triisocyanates and higher functionality isocyanates.

In certain embodiments, the component comprising at least two isocyanate groups comprises at least one of hexamethylene diisocyanate (HDI), isophorone diisocyanate (IPDI), methylene diphenyl diisocyanate (MDI), toluene diisocyanate (TDI), phenylene diisocyanate, naphthalene diisocyanate, diphenyl sulfone diisocyanate, ethylene diisocyanate, propylene diisocyanate, dimers of these diisocyanates, trimers of these diisocyanates, triphenylmethane triisocyanate, polyphenylmethane polyisocyanate (polymeric MDI), or mixtures thereof.

In certain embodiments, a method of preparing the dual curable composition is provided, the method comprising:

reacting a component comprising at least two isocyanate groups with a hydroxyacrylate and a mercaptosilane to form a reaction product comprising at least one acrylate group and at least one silane group.

In certain embodiments, a method of preparing the dual curable composition is provided, the method comprising:

reacting a hydroxyl-functional component comprising at least two hydroxyl groups with an isocyanatoacrylate and an isocyanatosilane to form a reaction product comprising at least one acrylate group and at least one silane group.

In certain embodiments, a method of preparing the dual curable composition is provided, the method comprising:

reacting an amine-functional component comprising at least two amine groups with an isocyanatoacrylate and an isocyanatosilane to form a reaction product comprising at least one acrylate group and at least one silane group.

In certain embodiments, a method of preparing the dual curable composition is provided, the method comprising:

reacting an amino-hydroxy-functional component comprising at least one amine group and one hydroxyl group with an isocyanatoacrylate and an isocyanatosilane to form a reaction product comprising at least one acrylate group and at least one silane group.

In certain embodiments, a method of preparing the dual curable composition is provided, the method comprising:

reacting an aminosilane with an isocyanatoacrylate to form a reaction product comprising at least one acrylate group and at least one silane group.

In other embodiments, the dual curable composition is prepared from at least one silane and/or acrylate, and at least one monomer, oligomer, polymer, or mixtures thereof by any method known to those of skill in the art.

A method of coating a substrate is provided, comprising applying to the substrate the dual curable composition, and optionally exposing the coated substrate to a radiation source to cure the coating composition, wherein the radiation source is at least one of ultraviolet radiation or electron beam radiation.

For purposes of illustration but not by way of limitation, a method of coating a substrate is provided, wherein the applying to the substrate of the dual curable composition is at least one of spraying, brushing, rolling, squeegeeing, curtain coating, vacuum coating, spin coating, or any method of application known to those of skill in the art.

In certain embodiments, the method of coating a substrate comprises applying to the substrate the dual curable composition, and optionally exposing the coated substrate to a radiation source to cure the coating composition, wherein the radiation source is ultraviolet radiation.

In certain embodiments, ultraviolet (UV) radiation is provided by at least one of a mercury vapor lamp, doped mercury vapor lamp, pulsed xenon lamp, electroless lamp, LED lamps, sunlight, or a combination of sources. In some embodiments the UV radiation is provided by at least one of a microwave lamp H bulb, D bulb, Q bulb, or V bulb available from Heraeus Noblelight Fusion UV Inc, Gaithersburg, Md., used simultaneously or serially. In some embodiments, the UV radiation is provided by a handheld lamp suitable for field use.

Representative ultraviolet lamp systems are available from Heraeus Noblelight Fusion UV Inc., Gaithersburg, Md.; Nordson Corporation, Amherst, Ohio; American Ultraviolet®, Lebanon, Ind.; UV III Systems, Inc., Alburgh, Vt.; Jelight Company Inc., Irvine, Calif.; and H&S Autoshot, Niagara Falls, N.Y.

In certain embodiments, a method of coating a substrate with a two part coating comprising the dual curable composition is provided, comprising:
 a) Providing Part A and Part B;
 b) Mixing Part A and Part B to form a mixture;
 c) Applying the mixture to the substrate; and optionally
 d) Exposing the coated substrate to a radiation source to cure the mixture; wherein
 Part A comprises
  the dual curable composition; and
 Part B comprises at least one of:
  a corrosion inhibitor,
  an organic acid functional component,
  or mixtures thereof.

In certain embodiments, a method of coating a substrate with a two part coating comprising the dual curable composition is provided, comprising:
 a) Providing Part A and Part B;
 b) Mixing Part A and Part B to form a mixture;
 c) Applying the mixture to the substrate; and optionally
 d) Exposing the coated substrate to a radiation source to cure the mixture; wherein
 Part A further comprises at least one of
  a photoinitiator, reactive monomer, defoamer, dispersant, pigment,
  stabilizer, or mixtures thereof; and
 Part B further comprising at least one of:
  a dispersant, reactive monomer, defoamer, oligomer, adhesion
  promoter, surfactant, flow agent, or mixtures thereof.

In certain embodiments, a method of coating a substrate is provided, comprising applying to the substrate the dual curable composition, and allowing the coating composition to moisture cure in the absence of a radiation source.

In certain embodiments, a method of coating a substrate with the dual curable composition is provided, wherein the substrate is selected from the group consisting of metal, concrete, stone, vinyl, wood, tile, ceramic, glass, plastic, paper, cardboard, asphalt, thermoplastic materials, thermoset materials, rubber, and composite materials.

In certain embodiments, a method of coating a substrate with the dual curable composition is provided, wherein the substrate comprises a metal. In certain embodiments, the metal comprises aluminum, aluminum alloy, steel, stainless steel, magnesium alloy, or titanium.

In certain embodiments, a method of coating a substrate with the dual curable composition is provided, wherein the substrate comprises an industrial or aerospace substrate.

In certain embodiments, a corrosion-resistant coating, sealant, adhesive, or composite resin is provided, comprising the dual curable composition. In certain embodiments, a corrosion-resistant coating is provided, comprising the dual curable composition. In other embodiments, a corrosion-resistant sealant is provided, comprising the dual curable composition. In certain embodiments, a corrosion-resistant adhesive is provided, comprising the dual curable composition. In other embodiments, a corrosion-resistant composite resin is provided, comprising the dual curable composition.

In some embodiments, a solvent-free coating, sealant, adhesive, or composite resin is provided, comprising the dual curable composition. In some embodiments, an isocyanate-free coating, sealant, adhesive, or composite resin is provided, comprising the dual curable composition. In some embodiments, a chromium-free coating, sealant, adhesive, or composite resin is provided, comprising the dual curable composition.

In certain embodiments, a solvent-free, isocyanate-free, chromium-free coating, sealant, adhesive, or composite resin is provided, comprising the dual curable composition. In certain embodiments, a solvent-free, isocyanate-free, chromium-free coating is provided, comprising the dual curable composition. In other embodiments, a solvent-free, isocyanate-free, chromium-free sealant is provided, comprising the dual curable composition. In certain embodiments, a solvent-free, isocyanate-free, chromium-free adhesive is provided, comprising the dual curable composition. In other embodiments, a solvent-free, isocyanate-free, chromium-free composite resin is provided, comprising the dual curable composition.

In some embodiments, the dual curable composition is radiation-curable through the acrylate moiety for fast and efficient cure upon exposure to a radiation source which may comprise ultraviolet light. In some embodiments, the dual curable composition is capable of free radical addition polymerization through the double bond of the acrylate moiety.

In some embodiments, the dual curable composition is moisture curable through the silane moiety, activated by ambient moisture at ambient temperatures. While not being bound by theory, moisture cure may proceed through hydrolysis and condensation reactions of the organofunctional alkoxysilane moiety.

In some embodiments, the dual curable composition is radiation-cured with fast and efficient cure development of adhesion and hardness upon exposure to a radiation source. In some embodiments, cure development of adhesion and hardness continue through moisture cure after exposure to the radiation source is discontinued.

In some embodiments, the dual curable composition is cured under an ultraviolet light to a tack-free state with moderate hardness that permits a secondary operation such as sanding, before a higher degree of hardness develops through moisture cure for improved performance in extended use. The dual curable composition may be referred to as a hybrid material because it is curable by different reactions.

In some embodiments, the dual curable composition is cured using an ultraviolet light to a high degree of hardness that permits immediate masking of cured areas for subsequent operations, such as sanding and/or painting.

In some embodiments, tack-free cure of the dual curable composition is achieved in the absence of ultraviolet light. These embodiments are useful for the drying of the dual curable composition in shadow areas and for drying overspray from spraying operations.

In certain embodiments, the dual curable composition provides high performance properties throughout the bulk of at least one of a coating, sealant, adhesive, or composite resin. The high performance properties provided by the dual curable composition are suitable for industrial or aerospace applications.

In certain embodiments of the subject dual curable compositions, coatings, sealants, adhesives, composite resins, and methods, it may be desirable to omit certain compounds or components, in order to be free of such compounds or components as discussed below. In certain embodiments, being free of an additional component may result in savings with regard to the cost of the additional component and the time and logistics required for the addition of the component, and may also result in higher performance properties if the additional component would result in a dilution of properties.

In certain embodiments, it may be desirable to refrain from the use of a solvent. Dissolution in a solvent and evaporation of a solvent involve time and expense, and solvent evaporation may leave interstitial voids that can negatively impact properties. In certain embodiments, it may be desirable to omit colloidal silica in order to maintain certain appearance properties, to keep viscosity low, and to maintain homogeneity by preventing the possibility of agglomeration and crystallization of the colloidal silica.

In some embodiments, it may be desirable to omit the use of an acid which may alter the balance of functional groups, the balance of acidity and basicity, and overall stability, including stability of the silane groups since acidity accelerates hydrolysis. In certain embodiments, it may be desirable to omit the use of a curing catalyst which can introduce undesirable health considerations and can reduce stability.

In some embodiments, the silane of the dual curable composition is terminal. To avoid over-crosslinking that can result in diminished properties such as a loss of toughness and an increase in brittleness, in certain embodiments it may be desirable to omit the use of a bis silane, and in some embodiments it may be desirable to avoid internal chain segment silane structures. Internal silane structures may also have the disadvantage of lower reaction rates resulting from lower accessibility due to steric factors.

The following specific examples are provided to illustrate, but not limit, the dual curable composition, methods, coatings, sealants, adhesives and composite resins as discussed above.

Examples were prepared using acrylate monomers, CN2300 series hyperbranched polyester acrylates available from Sartomer Company, Exton, Pa., Ebecryl® oligomers available from Cytec Industries, Inc., Smyrna, Ga., Photomer® oligomers available from IGM Resins, Saint Charles, Ill., Desmolux® oligomers available from Bayer Corporation, Pittsburgh, Pa., aminosilanes, and epoxysilanes.

In a representative example, a dual curable composition was prepared by thorough mixing of an aminosilane and an acrylated component comprising at least two acrylate groups under dry desiccated air. The mixture was allowed to react at ambient temperature for at least 60 minutes to form a reaction product. In another representative example, the reaction product was thoroughly mixed with an epoxysilane under dry desiccated air, and allowed to react at ambient temperature for at least 60 minutes to form a second reaction product. The reaction products are dual curable compositions, and may be referred to as hybrid resins, and are designated in the examples by the acrylated starting material, the aminosilane, the epoxysilane, and the mole ratios used in their preparation. The dual curable compositions prepared are listed as Examples 1-117 in Tables 4-7 with hybrid resin (HR) designations for these and subsequent examples. In some examples, more than one hybrid resin is used, and for those examples the ratio of use is also reported.

In some of the specific examples, the dual curable composition further comprises an additional component of a curable composition. In some of the examples, the additional component is a photoinitiator. Other components are described below.

Two general UV cure protocols were used for examples. UV cure protocol 1 utilized a 300 W Fusion H bulb at a conveyor speed of 10 feet/minute. UV cure protocol 2 utilized 600 W Fusion V and H bulbs at a conveyor speed of 5 feet/minute. Testing was performed immediately after UV cure and at selected intervals following UV exposure.

Examples were applied at a 2 mil thickness and tested on A-36 aluminum panels available from Q-Lab, Cleveland, Ohio. Corrosion testing was performed for examples applied at a 2 mil thickness on 2024-T3 aluminum alloy panels treated with Alodine 1200S per MIL-C-5541 Type I Class 1A, available from Q-Lab, Cleveland, Ohio. Alodine® 1200S™ is a light metal conversion coating available from Henkel, Rocky Hill, Conn.

TABLE 1

| | Designation Of Aminosilanes For Examples |
|---|---|
| AS | Aminosilane |
| AS1 | delta-aminoneohexyltrimethoxysilane |
| AS2 | delta-aminoneohexylmethyldimethoxysilane |

TABLE 2

| | Designation Of Epoxysilanes For Examples |
|---|---|
| ES | Epoxysilane |
| ES1 | 3-glycidoxypropyltrimethoxysilane |
| ES2 | beta-(3,4-epoxycyclohexyl)ethyltrimethoxysilane |
| ES3 | beta-(3,4-epoxycyclohexyl)ethyl triethoxysilane |
| ES4 | 3-glycidoxypropylmethyldiethoxysilane |
| ES5 | 3-glycidoxypropyltriethoxysilane |

TABLE 3

Designation Of Acrylated Components For Examples

| AC | Acrylated Component |
|---|---|
| AC1 | CN2300 |
| AC2 | CN2302 |
| AC3 | CN2303 |
| AC4 | Trimethylolpropane Triacrylate |
| AC5 | Trimethylolpropane ethoxylate triacrylate |
| AC6 | Trimethylolpropane propoxylate triacrylate |
| AC7 | 1,6-Hexanedioldiacrylate |
| AC8 | Pentaerythritol ethoxylate tetraacrylate |
| AC9 | Photomer ® 6008 |
| AC10 | Photomer ® 6184 |
| AC11 | Photomer ® 6210 |
| AC12 | Photomer ® 6892 |
| AC13 | Ebecryl ® 4883 |
| AC14 | Desmolux ® U 100 |
| AC15 | Desmolux ® 2513 |
| AC16 | Desmolux ® 2666 |

TABLE 4

Dual Curable Composition Preparation Examples 1-35

| Example | HR | AC | AS | ES | AC/AS/ES |
|---|---|---|---|---|---|
| 1 | HR1 | AC1 | AS1 | ES1 | 1:1:1 |
| 2 | HR2 | AC1 | AS1 | ES1 | 1:2:2 |
| 3 | HR3 | AC1 | AS1 | ES1 | 1:3:3 |
| 4 | HR4 | AC1 | AS1 | ES1 | 1:4:4 |
| 5 | HR5 | AC2 | AS2 | ES3 | 1:4:4 |
| 6 | HR6 | AC2 | AS2 | ES3 | 1:8:8 |
| 7 | HR7 | AC2 | AS2 | ES3 | 1:12:12 |
| 8 | HR8 | AC2 | AS2 | ES3 | 1:1:1 |
| 9 | HR9 | AC2 | AS2 | ES3 | 1:2:2 |
| 10 | HR10 | AC2 | AS2 | ES3 | 1:3:3 |
| 11 | HR11 | AC2 | AS1 | ES1 | 1:1:1 |
| 12 | HR12 | AC2 | AS1 | ES1 | 1:2:2 |
| 13 | HR13 | AC2 | AS1 | ES1 | 1:3:3 |
| 14 | HR14 | AC2 | AS1 | ES1 | 1:4:4 |
| 15 | HR15 | AC3 | AS1 | ES1 | 1:1:1 |
| 16 | HR16 | AC3 | AS1 | ES1 | 1:2:2 |
| 17 | HR17 | AC3 | AS1 | ES1 | 1:3:3 |
| 18 | HR18 | AC3 | AS1 | ES1 | 1:4:4 |
| 19 | HR19 | AC4 | AS1 | ES1 | 1:0.2:0.2 |
| 20 | HR20 | AC4 | AS1 | ES1 | 1:0.4:0.4 |
| 21 | HR21 | AC4 | AS1 | ES1 | 1:0.6:0.6 |
| 22 | HR22 | AC4 | AS1 | ES1 | 1:0.8:0.8 |
| 23 | HR23 | AC4 | AS1 | ES1 | 1:1:1 |
| 24 | HR24 | AC4 | AS1 | ES1 | 1:1.2:1.2 |
| 25 | HR25 | AC4 | AS1 | ES1 | 1:1.4:1.4 |
| 26 | HR26 | AC4 | AS1 | ES1 | 1:1.6:1.6 |
| 27 | HR27 | AC4 | AS1 | ES1 | 1:1.8:1.8 |
| 28 | HR28 | AC4 | AS1 | ES1 | 1:2:2 |
| 29 | HR29 | AC5 | AS1 | ES1 | 1:0.2:0.2 |
| 30 | HR30 | AC5 | AS1 | ES1 | 1:0.4:0.4 |
| 31 | HR31 | AC5 | AS1 | ES1 | 1:0.6:0.6 |
| 32 | HR32 | AC5 | AS1 | ES1 | 1:0.8:0.8 |
| 33 | HR33 | AC5 | AS1 | ES1 | 1:1:1 |
| 34 | HR34 | AC5 | AS1 | ES1 | 1:1.2:1.2 |
| 35 | HR35 | AC5 | AS1 | ES1 | 1:1.4:1.4 |

TABLE 5

Dual Curable Composition Preparation Examples 36-70

| Example | HR | AC | AS | ES | AC/AS/ES |
|---|---|---|---|---|---|
| 36 | HR36 | AC5 | AS1 | ES1 | 1:1.6:1.6 |
| 37 | HR37 | AC5 | AS1 | ES1 | 1:1.8:1.8 |
| 38 | HR38 | AC5 | AS1 | ES1 | 1:2:2 |
| 39 | HR39 | AC6 | AS1 | ES1 | 1:0.2:0.2 |
| 40 | HR40 | AC6 | AS1 | ES1 | 1:0.4:0.4 |
| 41 | HR41 | AC6 | AS1 | ES1 | 1:0.6:0.6 |
| 42 | HR42 | AC6 | AS1 | ES1 | 1:0.8:0.8 |
| 43 | HR43 | AC6 | AS1 | ES1 | 1:1:1 |
| 44 | HR44 | AC6 | AS1 | ES1 | 1:1.2:1.2 |
| 45 | HR45 | AC6 | AS1 | ES1 | 1:1.4:1.4 |
| 46 | HR46 | AC6 | AS1 | ES1 | 1:1.6:1.6 |
| 47 | HR47 | AC6 | AS1 | ES1 | 1:1.8:1.8 |
| 48 | HR48 | AC6 | AS1 | ES1 | 1:2:2 |
| 49 | HR49 | AC7 | AS1 | ES1 | 1:0.2:0.2 |
| 50 | HR50 | AC7 | AS1 | ES1 | 1:0.4:0.4 |
| 51 | HR51 | AC7 | AS1 | ES1 | 1:0.6:0.6 |
| 52 | HR52 | AC7 | AS1 | ES1 | 1:0.8:0.8 |
| 53 | HR53 | AC7 | AS1 | ES1 | 1:1:1 |
| 54 | HR54 | AC8 | AS1 | ES1 | 1:0.2:0.2 |
| 55 | HR55 | AC8 | AS1 | ES1 | 1:0.4:0.4 |
| 56 | HR56 | AC8 | AS1 | ES1 | 1:0.6:0.6 |
| 57 | HR57 | AC8 | AS1 | ES1 | 1:0.8:0.8 |
| 58 | HR58 | AC8 | AS1 | ES1 | 1:1:1 |
| 59 | HR59 | AC8 | AS1 | ES1 | 1:1.2:1.2 |
| 60 | HR60 | AC8 | AS1 | ES1 | 1:1.4:1.4 |
| 61 | HR61 | AC8 | AS1 | ES1 | 1:1.6:1.6 |
| 62 | HR62 | AC8 | AS1 | ES1 | 1:1.8:1.8 |
| 63 | HR63 | AC8 | AS1 | ES1 | 1:2:2 |
| 64 | HR64 | AC9 | AS1 | ES1 | 1:0.25:0.25 |
| 65 | HR65 | AC9 | AS1 | ES1 | 1:0.5:0.5 |
| 66 | HR66 | AC9 | AS1 | ES1 | 1:0.75:0.75 |
| 67 | HR67 | AC9 | AS1 | ES1 | 1:1:1 |
| 68 | HR68 | AC9 | AS1 | ES1 | 1:1.25:1.25 |
| 69 | HR69 | AC9 | AS1 | ES1 | 1:1.5:1.5 |
| 70 | HR70 | AC9 | AS1 | ES1 | 1:1.75:1.75 |

TABLE 6

Dual Curable Composition Preparation Examples 71-105

| Example | HR | AC | AS | ES | AC/AS/ES |
|---|---|---|---|---|---|
| 71 | HR71 | AC9 | AS1 | ES1 | 1:2:2 |
| 72 | HR72 | AC10 | AS1 | ES1 | 1:0.25:0.25 |
| 73 | HR73 | AC10 | AS1 | ES1 | 1:0.5:0.5 |
| 74 | HR74 | AC10 | AS1 | ES1 | 1:0.75:0.75 |
| 75 | HR75 | AC10 | AS1 | ES1 | 1:1:1 |
| 76 | HR76 | AC10 | AS1 | ES1 | 1:1.25:1.25 |
| 77 | HR77 | AC10 | AS1 | ES1 | 1:1.5:1.5 |
| 78 | HR78 | AC10 | AS1 | ES1 | 1:1.75:1.75 |
| 79 | HR79 | AC10 | AS1 | ES1 | 1:2:2 |
| 80 | HR80 | AC10 | AS1 | ES1 | 1:0.25:0.5 |
| 81 | HR81 | AC10 | AS1 | ES1 | 1:0.5:1 |
| 82 | HR82 | AC10 | AS1 | ES1 | 1:0.75:1.5 |
| 83 | HR83 | AC10 | AS1 | ES1 | 1:1:2 |
| 84 | HR84 | AC10 | AS1 | ES1 | 1:1.25:2.5 |
| 85 | HR85 | AC10 | AS1 | ES1 | 1:1.5:3 |
| 86 | HR86 | AC11 | AS1 | ES1 | 1:0.2:0.2 |
| 87 | HR87 | AC11 | AS1 | ES1 | 1:0.4:0.4 |
| 88 | HR88 | AC11 | AS1 | ES1 | 1:0.6:0.6 |
| 89 | HR89 | AC11 | AS1 | ES1 | 1:0.8:0.8 |
| 90 | HR90 | AC11 | AS1 | ES1 | 1:1:1 |
| 91 | HR91 | AC12 | AS1 | ES1 | 1:0.2:0.2 |
| 92 | HR92 | AC12 | AS1 | ES1 | 1:0.4:0.4 |
| 93 | HR93 | AC12 | AS1 | ES1 | 1:0.5:0.5 |
| 94 | HR94 | AC12 | AS1 | ES1 | 1:0.6:0.6 |
| 95 | HR95 | AC12 | AS1 | ES1 | 1:0.8:0.8 |
| 96 | HR96 | AC12 | AS1 | ES1 | 1:1:1 |
| 97 | HR97 | AC12 | AS1 | ES1 | 1:1.2:1.2 |
| 98 | HR98 | AC12 | AS1 | ES1 | 1:1.4:1.4 |
| 99 | HR99 | AC12 | AS1 | ES1 | 1:1.5:1.5 |
| 100 | HR100 | AC12 | AS1 | ES1 | 1:1.6:1.6 |
| 101 | HR101 | AC12 | AS1 | ES1 | 1:1.8:1.8 |
| 102 | HR102 | AC12 | AS1 | ES1 | 1:2:2 |
| 103 | HR103 | AC13 | AS1 | ES1 | 1:0.5:0.5 |
| 104 | HR104 | AC13 | AS1 | ES1 | 1:1:1 |
| 105 | HR105 | AC13 | AS1 | ES1 | 1:1.5:1.5 |

TABLE 7

Dual Curable Composition Preparation Examples 106-117

| Example | HR | AC | AS | ES | AC/AS/ES |
|---|---|---|---|---|---|
| 106 | HR106 | AC14 | AS1 | ES1 | 1:0.5:0.5 |
| 107 | HR107 | AC14 | AS1 | ES1 | 1:1:1 |
| 108 | HR108 | AC15 | AS1 | ES1 | 1:1:1 |
| 109 | HR109 | AC16 | AS1 | ES1 | 1:1:1 |
| 110 | HR110 | AC16 | AS1 | ES1 | 1:2:2 |
| 111 | HR111 | AC9 | AS1 | ES3 | 1:1:1 |
| 112 | HR112 | AC9 | AS1 | ES5 | 1:1:1 |
| 113 | HR113 | AC9 | AS2 | ES1 | 1:1:1 |
| 114 | HR114 | AC9 | AS2 | ES2 | 1:1:1 |
| 115 | HR115 | AC9 | AS2 | ES3 | 1:1:1 |
| 116 | HR116 | AC9 | AS2 | ES4 | 1:1:1 |
| 117 | HR117 | AC9 | AS2 | ES5 | 1:1:1 |

For Examples 120-128, dual curable compositions prepared in earlier examples were mixed with 5% benzophenone/1-hydroxy cyclohexyl phenyl ketone (1:1) photoinitiator, applied to aluminum panels, and subjected to UV cure protocol 1. Table 8 lists adhesion measurements at various time intervals. Measurements made immediately after UV exposure are referred to as "immediate" or "$T_o$" measurements. For Example 120, the behavior of a non-silylated acrylated compound is presented as a control to demonstrate the improved performance provided by the dual curable compositions. With the same amount of photoinitiator and UV exposure, the adhesion property of the "non-HR" compound is inferior.

TABLE 8

Adhesion Properties For Examples 120-128

| Example | HR | Immediate | 1 Day | 2 Days | 3 Days | 4 Days | 5 Days | 6 Days | 7 Days |
|---|---|---|---|---|---|---|---|---|---|
| 120 | AC12 | 0B | 0B | 0B | 0B | 0B | 0B | 0B | 0B |
| 121 | HR94 | 0B | 0B | 0B | 2B | 2B | 5B | 5B | 5B |
| 122 | HR95 | 0B | 0B | 1B | 3B | 3B | 5B | 5B | 5B |
| 123 | HR96 | 0B | 0B | 1B | 3B | 5B | 5B | 5B | 5B |
| 124 | HR97 | 0B | 0B | 2B | 3B | 5B | 5B | 5B | 5B |
| 125 | HR98 | 0B | 1B | 3B | 4B | 5B | 5B | 5B | 5B |
| 126 | HR100 | 0B | 1B | 3B | 4B | 5B | 5B | 5B | 5B |
| 127 | HR101 | 0B | 1B | 4B | 4B | 5B | 5B | 5B | 5B |
| 128 | HR102 | 0B | 1B | 3B | 4B | 5B | 5B | 5B | 5B |

For Examples 129-134, a mixed photoinitiator system of benzophenone/1-hydroxy cyclohexyl phenyl ketone (1:1) and a 50% solution of triarylsulfonium hexafluorophosphate in propylene carbonate was added to the dual curable composition HR96 in equal amounts, applied to aluminum panels, and subjected to UV cure protocol 1. Total amounts of photoinitiator (PI) are listed in Table 9 which also lists adhesion measurements at various time intervals.

TABLE 9

Adhesion Properties For Examples 129-134

| | Example: | | | | | |
|---|---|---|---|---|---|---|
| Time: | 129 1% PI | 130 2% PI | 131 3% PI | 132 4% PI | 133 5% PI | 134 10% PI |
| 1 hr | 0B | 0B | 0B | 0B | 0B | 0B |
| 2 hrs | 2B | 0B | 0B | 0B | 0B | 0B |
| 3 hrs | 2B | 2B | 0B | 1B | 1B | 0B |
| 4 hrs | 3B | 1B | 1B | 1B | 1B | 1B |
| 5 hrs | 2B | 1B | 1B | 1B | 1B | 1B |
| 6 hrs | 2B | 1B | 1B | 1B | 1B | 1B |
| 7 hrs | 2B | 1B | 2B | 1B | 1B | 1B |
| 8 hrs | 2B | 1B | 1B | 1B | 2B | 2B |
| 16 hrs | 3B | 2B | 3B | 4B | 3B | 3B |
| 24 hrs | 3B | 2B | 2B | 3B | 3B | 3B |
| 28 hrs | 3B | 2B | 2B | 3B | 3B | 3B |
| 32 hrs | 4B | 3B | 3B | 3B | 3B | 3B |
| 42 hrs | 5B | 4B | 4B | 5B | 5B | 5B |
| 58 hrs | 5B | 5B | 5B | 5B | 5B | 5B |

Examples 135-142 were mixed according to Formulation 1, applied to aluminum panels, and subjected to UV cure protocol 2. Example 135 represents a control with a non-silylated acrylated compound. Adhesion results for the examples are shown in Table 10, and pencil hardness results for the same examples are shown in Table 11. Measurements made immediately after UV exposure are referred to as "immediate" or "$T_o$" measurements. Inferior adhesion properties of the non-silylated acrylated compound control demonstrate the improved performance provided by the dual curable compositions.

Formulation 1

| | Parts |
|---|---|
| Dual Curable Composition (Or Control Acrylate) | 50.0 |
| Defoamer | 0.5 |
| Corrosion Inhibitor | 29.0 |
| Isobornyl Acrylate | 8.5 |
| Titanium Dioxide | 1.9 |
| Black Pigment | 0.3 |
| Synthetic Amorphous Silica | 5.0 |
| Photoinitiator | 3.8 |
| Triarylsulfonium Hexafluorophosphate (50% in propylenecarbonate) | 1 |
| Total | 100.0 |

TABLE 10

Adhesion Properties For Gray Coatings For Examples 135-142

| Example | HR | $T_o$ | 1 Hour | 2 Hours | 3 Hours | 24 Hours |
|---|---|---|---|---|---|---|
| 135 | AC10 | 0B | 0B | 0B | 0B | 0B |
| 136 | HR73 | 5B | 5B | 5B | 5B | 5B |
| 137 | HR74 | 4B | 5B | 5B | 5B | 5B |
| 138 | HR75 | 4B | 4B | 5B | 5B | 5B |
| 139 | HR76 | 4B | 5B | 4B | 5B | 5B |
| 140 | HR77 | 5B | 5B | 4B | 4B | 5B |
| 141 | HR78 | 4B | 5B | 4B | 5B | 5B |
| 142 | HR79 | 5B | 5B | 5B | 5B | 5B |

TABLE 11

Pencil Hardness Properties For Gray Coatings For Examples 135-142

| Example | HR | 1 Hour | 2 Hours | 3 Hours | 24 Hours |
|---|---|---|---|---|---|
| 135 | AC10 | 6H | 8H | 9H | 9H |
| 136 | HR73 | 6H | 7H | 7H | 9H |

TABLE 11-continued

Pencil Hardness Properties For Gray Coatings For Examples 135-142

| Example | HR | 1 Hour | 2 Hours | 3 Hours | 24 Hours |
|---|---|---|---|---|---|
| 137 | HR74 | H | 7H | 7H | 9H |
| 138 | HR75 | F | 2H | 4H | 9H |
| 139 | HR76 | 2B | HB | H | 7H |
| 140 | HR77 | 2B | 2B | F | 7H |
| 141 | HR78 | 6B | 2B | HB | 6H |
| 142 | HR79 | <9B | 7B | 2B | 6H |

Examples 143-149 were mixed according to Formulation 2, with the percentage of dispersant and corrosion inhibitor increasing in a stepwise fashion and the percentages of monomers and oligomer decreasing accordingly across the series. Weight % corrosion inhibitor increased across the series from 0% to 30% in 5% increments. The concentration of dual curable composition remained the same throughout the series. Part A and Part B for each example were mixed together, applied to aluminum panels for physical property testing and to 2024-T3 aluminum alloy panels for salt fog testing, and subjected to UV cure protocol 2. Results for the examples are shown in Tables 12-15.

Formulation 2

|  | Parts | | Parts |
|---|---|---|---|
| Part A | | | |
| Dual Curable Composition | 39.15 | | 39.15 |
| Defoamer | 0.15 | | 0.15 |
| Isobornyl Acrylate | 1.70 | | 1.70 |
| Polymeric Dispersant | 0.25 | | 0.25 |
| Titanium Dioxide | 1.50 | | 1.50 |
| Black Pigment | 0.25 | | 0.25 |
| Hydoxyphenyltriazine Stabilizer | 2.00 | | 2.00 |
| Photoinitiator | 5.00 | | 5.00 |
| Part B | | | |
| Hexanediol Propoxylate Diacrylate | 8.00 | to | 2.00 |
| Isobornyl Acrylate | 30.50 | to | 9.50 |
| Urethane Acrylate | 8.55 | to | 4.05 |
| Dispersant | 0.00 | to | 1.50 |
| Defoamer | 0.15 | | 0.15 |
| Corrosion Inhibitor | 0.00 | to | 30.00 |
| Substrate Wetting Additive | 0.30 | | 0.30 |
| Adhesion Promoter | 2.50 | | 2.50 |
| Total | 100.00 | | 100.00 |

TABLE 12

Adhesion Properties For Two Part Gray Coatings For Examples 143-149

| Example | HR | % Inhibitor | Immediate | 24 Hours | 7 Days |
|---|---|---|---|---|---|
| 143 | HR67 | 0.0 | 5B | 5B | 5B |
| 144 | HR67 | 5.0 | 5B | 5B | 5B |
| 145 | HR67 | 10.0 | 5B | 5B | 5B |
| 146 | HR67 | 15.0 | 5B | 5B | 5B |
| 147 | HR67 | 20.0 | 5B | 5B | 5B |
| 148 | HR67 | 25.0 | 5B | 5B | 5B |
| 149 | HR67 | 30.0 | 5B | 5B | 5B |

TABLE 13

Hardness Properties For Two Part Gray Coatings For Examples 143-149

| Example | HR | % Inhibitor | Immediate | 24 Hours | 7 Days |
|---|---|---|---|---|---|
| 143 | HR67 | 0.0 | 9H | 9H | 9H |
| 144 | HR67 | 5.0 | 9H | 9H | 9H |
| 145 | HR67 | 10.0 | 9H | 9H | 9H |
| 146 | HR67 | 15.0 | 9H | 9H | 9H |
| 147 | HR67 | 20.0 | 9H | 9H | 9H |
| 148 | HR67 | 25.0 | 9H | 9H | 9H |
| 149 | HR67 | 30.0 | 9H | 9H | 9H |

TABLE 14

Solvent Resistance Properties For Examples 143-149

| Example | HR | % Inhibitor | MEK Double Rubs | Pencil Hardness | After 24 Hrs Skydrol ® |
|---|---|---|---|---|---|
| 143 | HR67 | 0.0 | >200 | 9H | 9H |
| 144 | HR67 | 5.0 | >200 | 9H | 9H |
| 145 | HR67 | 10.0 | >200 | 9H | 9H |
| 146 | HR67 | 15.0 | >200 | 9H | 9H |
| 147 | HR67 | 20.0 | >200 | 9H | 9H |
| 148 | HR67 | 25.0 | >200 | 9H | 9H |
| 149 | HR67 | 30.0 | >200 | 9H | 9H |

TABLE 15

Corrosion Resistance Properties For Examples 143-149

| Example | HR | % Inh | 500 Hr | 1000 Hr | 1500 Hr | 2000 Hr | 2500 Hr | 3000 Hr |
|---|---|---|---|---|---|---|---|---|
| 143 | HR67 | 0.0 | E | P | P | P | P | P |
| 144 | HR67 | 5.0 | E | G | P | P | P | P |
| 145 | HR67 | 10.0 | E | G | P | P | P | P |
| 146 | HR67 | 15.0 | E | E | G | F | P | P |
| 147 | HR67 | 20.0 | E | E | G | G | F | P |
| 148 | HR67 | 25.0 | E | E | E | G | F | F |
| 149 | HR67 | 30.0 | E | E | E | G | F | F |

Examples 150-152 were mixed according to Formula 3. Results for the examples are shown in Tables 16-19.

Formulation 3

|  | Parts |
|---|---|
| Part A | |
| Dual Curable Composition Blend | 39.15 |
| Defoamer | 0.15 |
| Isobornyl Acrylate | 1.75 |
| Polymeric Dispersant | 0.25 |
| Titanium Dioxide | 1.50 |
| Black Pigment | 0.20 |
| Hydroxyphenyltriazine Stabilizer | 2.00 |
| Photoinitiator | 5.00 |
| Part B | |
| Hexanediol Propoxylate Diacrylate | 3.42 |
| Isobornyl Acrylate | 12.90 |
| Urethane Acrylate | 4.48 |
| Polymeric Dispersant | 1.25 |
| Defoamer | 0.15 |
| Corrosion Inhibitor | 25.00 |
| Substrate Wetting Additive | 0.30 |
| Adhesion Promoter | 2.50 |
| Total | 100.00 |

TABLE 16

Adhesion Properties For Two Part Gray Coatings For Examples 150-152

| Example | HR Blend | Ratio | % Inhibitor | Immediate | 24 Hours | 7 Days |
|---|---|---|---|---|---|---|
| 150 | HR67:HR109 | 3:1 | 25.0 | 5B | 5B | 5B |
| 151 | HR67:HR110 | 1:1 | 25.0 | 4B | 5B | 5B |
| 152 | HR67:HR69 | 1:3 | 25.0 | 4B | 5B | 4B |

TABLE 17

Hardness Properties For Two Part Gray Coatings For Examples 150-152

| Example | HR Blend | Ratio | % Inhibitor | Immediate | 24 Hours | 7 Days |
|---|---|---|---|---|---|---|
| 150 | HR67:HR109 | 3:1 | 25.0 | 2H | 6H | 6H |
| 151 | HR67:HR110 | 1:1 | 25.0 | B | HB | 6H |
| 152 | HR67:HR69 | 1:3 | 25.0 | 4H | 4H | 8H |

TABLE 18

Solvent Resistance Properties For Examples 150-152

| Example | HR Blend | Ratio | % Inhibitor | MEK Double Rubs | Pencil Hardness | After 24 Hrs Skydrol® |
|---|---|---|---|---|---|---|
| 150 | HR67:HR109 | 3:1 | 25.0 | >200 | 6H | 6H |
| 151 | HR67:HR109 | 1:1 | 25.0 | >200 | 6H | 6H |
| 153 | HR67:HR69 | 1:3 | 25.0 | >200 | 8H | 8H |

TABLE 19

Corrosion Resistance Properties For Examples 150-152

| Ex | Blend | Ratio | 500 Hr | 1000 Hr | 1500 Hr | 2000 Hr | 2500 Hr | 3000 Hr |
|---|---|---|---|---|---|---|---|---|
| 150 | HR67:HR109 | 3:1 | E | E | E | E | E | F |
| 151 | HR67:HR110 | 1:1 | E | E | E | E | E | E |
| 152 | HR67:HR69 | 1:3 | E | E | E | E | E | E |

Adhesion was evaluated using the standard paint adhesion test method ASTM D3359 Standard Test Methods for Measuring Adhesion by Tape Test. Using this crosshatch adhesion test method, a rating of 5B is given to the sample if the edges of the cuts are completely smooth and none of the squares of the lattice is detached, therefore 100% adhesion and 0% adhesion failure. A rating of 4B applies if small flakes of the coating are detached at intersections of cuts, and less than 5% of the area is affected, therefore 5% adhesion failure. A rating of 3B applies if small flakes of the coating are detached along edges and at intersections of cuts, and the adhesion failure area is 5 to 15% of the lattice. A rating of 2B applies if the coating has flaked along the edges and on parts of the squares, and the adhesion failure area is 15 to 35% of the lattice. A rating of 1B applies if the coating has flaked along the edges of cuts in large ribbons and whole squares have detached, and the adhesion failure area is 35 to 65% of the lattice. A rating of 0B applies if flaking and detachment is worse than Grade 1B, corresponding to adhesion failure area of greater than 65% of the lattice.

Pencil hardness was evaluated using ASTM Test Method D 3363, and was recorded as the hardest pencil that will not cut into or gouge the film. Solvent resistance was tested 7 days after UV exposure, and excellent solvent resistance for numerous cured examples was demonstrated by resistance to over 200 methyl ethyl ketone (MEK) double rubs, and by virtue of maintaining integrity and hardness after 24 hours of soaking in Skydrol® LD-4 hydraulic fluid available from Solutia, St. Louis, Mo.

Corrosion resistance testing in salt-fog up to 3000 hours was performed on scribed 2024-T3 aluminum alloy panels according to ASTM Test Method B-117, and rated according to the following parameters: A rating of excellent (E) corresponds to a panel with scribe lines that remain shiny or have only a small amount of darkening on a panel with no white salt or blisters or creepage of the scribe lines, a rating of good (G) corresponds to a panel with scribe lines that exhibit darkening of about 50% or more on a panel that is almost completely free from white salt or blisters or creepage of the scribe lines, a rating of fair (F) corresponds to a panel with a scribe lines that are dark on a panel that has several localized sites of white salt in the scribe lines and/or has a few blisters and/or exhibits some creepage of the scribe lines, and a rating of poor (P) corresponds to a panel with scribe lines that are completely darkened on a panel that has white salt filling the scribe lines and/or has many blisters and/or exhibits significant creepage of the scribe lines.

It will be understood that the embodiments described herein are merely exemplary, and that one skilled in the art may make variations and modifications without departing from the spirit and scope of the embodiments. All such variations and modifications are intended to be included within the scope of the embodiments as described hereinabove. Further, all embodiments disclosed are not necessarily in the alternative, as various embodiments may be combined to provide the desired result.

I claim:

1. A dual curable composition, comprising an acrylate and a compound represented by formula (I):

$$(\text{acrylate})_a\text{-(A)-(silane)}_b \quad (I)$$

in which a and b are identical or different and are each represented by an integer greater than or equal to 1; and wherein the dual curable composition is further represented by formula (IV) and/or formula (V):

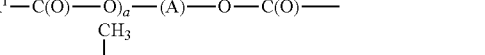
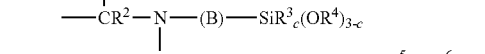

in which
a is represented by an integer greater than or equal to 1;
c is an integer equal to 0, 1, or 2;
d is an integer equal to 0, 1, or 2;
the moiety A comprises at least one of an aliphatic hydrocarbon, a cycloaliphatic hydrocarbon, an aryl moiety, an ether, an ester, an amide, a urethane, a urea, a hydroxyl group-containing organic moiety, an acrylic oligomer, an epoxy oligomer, a urethane oligomer, a polyester oligomer, or mixtures thereof;

the moiety B comprises at least one of an aliphatic hydrocarbon, a cycloaliphatic hydrocarbon, an aryl moiety, an ether, an amide, or mixtures thereof;
wherein the moiety B has a molecular weight less than or equal to 500;
the moiety D comprises at least one of an aliphatic hydrocarbon, a cycloaliphatic hydrocarbon, an aryl moiety, an ether, or mixtures thereof;
wherein the moiety D has a molecular weight less than or equal to 500;
$R^1$ and $R^2$ are each independently H or an alkyl group having 1 to about 8 C atoms; and
$R^3$, $R^4$, $R^5$, and $R^6$ are each independently alkyl groups having 1 to about 8 C atoms;
wherein the dual curable composition has a molecular weight greater than or equal to 500; and
wherein the dual curable composition is radiation-curable and/or moisture curable.

2. The dual curable composition of claim 1, further comprising an additional component of a curable composition.

3. The dual curable composition of claim 1, further comprising a silane.

4. The dual curable composition of claim 1, further comprising a reactive monomer.

5. The dual curable composition of claim 1, further comprising an oligomer.

6. The dual curable composition of claim 1, further comprising a photoinitiator.

7. The dual curable composition of claim 1, further comprising a cationic photoinitiator.

8. The dual curable composition of claim 1, further comprising at least one of a dispersant, pigment, filler, flow agent, leveling agent, wetting agent, surfactant, defoamer, rheology modifier, stabilizer, antioxidant, adhesion promoter, corrosion inhibitor, or mixtures thereof.

9. The dual curable composition of claim 1, wherein the moiety A comprises at least one of an ester, an amide, a urethane, a urea, an acrylic oligomer, a urethane oligomer, a polyester oligomer, or mixtures thereof.

10. The dual curable composition of claim 9, wherein the moiety A comprises at least one of an ester, an amide, a urethane, a urea, or mixtures thereof.

11. The dual curable composition of claim 9, wherein the moiety A comprises at least one of an acrylic oligomer, a urethane oligomer, a polyester oligomer, or mixtures thereof.

12. The dual curable composition of claim 11, wherein the moiety A comprises a urethane oligomer.

13. The dual curable composition of claim 11, wherein the moiety A comprises a polyester oligomer.

14. A coating, sealant, adhesive, or composite resin comprising the dual curable composition of claim 1.

15. A corrosion-resistant coating, sealant, adhesive, or composite resin comprising the dual curable composition of claim 1.

16. A solvent-free, isocyanate-free, chromium-free coating, sealant, adhesive, or composite resin comprising the dual curable composition of claim 1.

17. A two part coating, sealant, adhesive, or composite resin comprising Part A and Part B;
Part A comprising:
the dual curable composition of claim 1; and
Part B comprising at least one of:
a corrosion inhibitor,
an organic acid functional component,
or mixtures thereof.

18. The two part coating, sealant, adhesive, or composite resin of claim 17;
Part A further comprising at least one of:
a photoinitiator, reactive monomer, defoamer, dispersant, pigment, stabilizer, or mixtures thereof; and
Part B further comprising at least one of:
a dispersant, reactive monomer, defoamer, oligomer, adhesion promoter, surfactant, flow agent, or mixtures thereof.

19. A method of preparing the composition of claim 1, the method comprising:
reacting an acrylated component comprising at least two acrylate groups with an aminosilane to form a reaction product comprising at least one acrylate group and at least one silane group;
reacting an epoxysilane with the reaction product comprising at least one acrylate group and at least one silane group to form a second reaction product comprising at least one acrylate group and at least two silane groups;
contacting an acrylate with the second reaction product comprising at least one acrylate group and at least two silane groups; and
optionally further comprising contacting an additional component of a curable composition with the second reaction product comprising at least one acrylate group and at least two silane groups.

20. The method according to claim 19, wherein the acrylated component comprises at least one of a diacrylate monomer, aliphatic polyether urethane diacrylate, aliphatic polyester urethane diacrylate, aromatic polyether urethane diacrylate, aromatic polyester urethane diacrylate, polyester diacrylate, polyether diacrylate, epoxy diacrylate, acrylated acrylic diacrylate, polyacrylate monomer, aliphatic polyether urethane polyacrylate, aliphatic polyester urethane polyacrylate, aromatic polyether urethane polyacrylate, aromatic polyester urethane polyacrylate, polyester polyacrylate, polyether polyacrylate, epoxy polyacrylate, acrylated acrylic polyacrylate, acrylate grafted polymer, acrylated polyolefin, acrylated polytetrafluoroethylene, acrylated polyester, acrylated polyamide, or mixtures thereof.

21. The method according to claim 19, wherein the aminosilane comprises at least one of 3-aminopropyltrimethoxysilane, 3-aminopropyltriethoxysilane, N-beta-(aminoethyl)-3-aminopropyltrimethoxysilane, N-beta-(aminoethyl)-3-aminopropyl methyldimethoxysilane, N-beta-(aminoethyl)-3-aminopropyltriethoxysilane, delta-aminoneohexyltrimethoxysilane, delta-aminoneohexylmethyldimethoxysilane, delta-aminoneohexyl triethoxysilane, or mixtures thereof.

22. The method according to claim 19, wherein the epoxysilane comprises at least one of 3-glycidoxypropyltrimethoxysilane, 3-glycidoxypropyltriethoxysilane, 3-glycidoxypropyl methyldimethoxysilane, 3-glycidoxypropylmethyldiethoxysilane, beta-(3,4-epoxycyclohexyl)ethyltrimethoxysilane, beta-(3,4-epoxycyclohexyl)ethyl triethoxysilane, or mixtures thereof.

23. The method of claim 19, wherein the additional component of a curable composition comprises at least one of a silane, a reactive monomer, an oligomer, a photoinitiator, cationic photoinitiator, dispersant, pigment, filler, flow agent, leveling agent, wetting agent, surfactant, defoamer, rheology modifier, stabilizer, antioxidant, adhesion promoter, corrosion inhibitor, or mixtures thereof.

24. A method of coating a substrate comprising applying to the substrate the dual curable composition of claim 1, and optionally exposing the coated substrate to a radiation source to cure the coating composition, wherein the radiation source is at least one of ultraviolet radiation or electron beam radiation.

25. The method of claim 24, wherein the substrate is selected from the group consisting of metal, concrete, stone, vinyl, wood, tile, ceramic, glass, plastic, paper, cardboard, asphalt, thermoplastic materials, thermoset materials, rubber, and composite materials.

26. The method of claim 24, wherein the substrate comprises a metal.

27. The method of claim 26, wherein the metal comprises aluminum, aluminum alloy, steel, stainless steel, magnesium alloy, or titanium.

28. The method of claim 24, wherein the substrate comprises an industrial or aerospace substrate.

29. A method of coating a substrate with the two part coating of claim 17, comprising:
a) Providing Part A and Part B;
b) Mixing Part A and Part B to form a mixture;
c) Applying the mixture to the substrate; and optionally
d) Exposing the coated substrate to a radiation source to cure the mixture.

30. A method of coating a substrate with the two part coating of claim 18, comprising:
a) Providing Part A and Part B;
b) Mixing Part A and Part B to form a mixture;
c) Applying the mixture to the substrate; and optionally
d) Exposing the coated substrate to a radiation source to cure the mixture.

31. A dual curable composition, comprising a photoinitiator and a compound represented by formula (I):

$$(\text{acrylate})_a\text{-(A)-(silane)}_b \qquad (\text{I})$$

in which a and b are identical or different and are each represented by an integer greater than or equal to 1; and wherein the dual curable composition is further represented by formula (IV) and/or formula (V):

$$(CH_2{=}CR^1{-}C(O){-}O)_a{-}(A){-}O{-}C(O){-}CHR^2{-}CH_2{-}N{-}(B){-}SiR^3_c(OR^4)_{3-c} \qquad (IV)$$
$$\phantom{xxxxxxxxxxxxxxxxxxxxxxxxxxxxxxxxxxxxxxxxxxxx}|$$
$$\phantom{xxxxxxxxxxxxxxxxxxxxxxxxxxxxxxxxxxxxxx}CH_2{-}CH(OH){-}(D){-}SiR^5_d(OR^6)_{3-d}$$

$$(CH_2{=}CR^1{-}C(O){-}O)_a{-}(A){-}O{-}C(O){-}CR^2(CH_3){-}N{-}(B){-}SiR^3_c(OR^4)_{3-c} \qquad (V)$$
$$\phantom{xxxxxxxxxxxxxxxxxxxxxxxxxxxxxxxxxxxxxxxxxxxx}|$$
$$\phantom{xxxxxxxxxxxxxxxxxxxxxxxxxxxxxxxxxxxxxx}CH_2{-}CH(OH){-}(D){-}SiR^5_d(OR^6)_{3-d}$$

in which
a is represented by an integer greater than or equal to 1;
c is an integer equal to 0, 1, or 2;
d is an integer equal to 0, 1, or 2;
the moiety A comprises at least one of an aliphatic hydrocarbon, a cycloaliphatic hydrocarbon, an aryl moiety, an ether, an ester, an amide, a urethane, a urea, a hydroxyl group-containing organic moiety, an acrylic oligomer, an epoxy oligomer, a urethane oligomer, a polyester oligomer, or mixtures thereof;
the moiety B comprises at least one of an aliphatic hydrocarbon, a cycloaliphatic hydrocarbon, an aryl moiety, an ether, an amide, or mixtures thereof;
wherein the moiety B has a molecular weight less than or equal to 500;
the moiety D comprises at least one of an aliphatic hydrocarbon, a cycloaliphatic hydrocarbon, an aryl moiety, an ether, or mixtures thereof;

wherein the moiety D has a molecular weight less than or equal to 500;
$R^1$ and $R^2$ are each independently H or an alkyl group having 1 to about 8 C atoms; and
$R^3$, $R^4$, $R^5$, and $R^6$ are each independently alkyl groups having 1 to about 8 C atoms;
wherein the dual curable composition has a molecular weight greater than or equal to 500; and
wherein the dual curable composition is radiation-curable and/or moisture curable.

32. The dual curable composition of claim 31, further comprising an additional component of a curable composition.

33. The dual curable composition of claim 31, further comprising a silane.

34. The dual curable composition of claim 31, further comprising a reactive monomer.

35. The dual curable composition of claim 31, further comprising an oligomer.

36. The dual curable composition of claim 31, further comprising a cationic photoinitiator.

37. The dual curable composition of claim 31, further comprising at least one of a dispersant, pigment, filler, flow agent, leveling agent, wetting agent, surfactant, defoamer, rheology modifier, stabilizer, antioxidant, adhesion promoter, corrosion inhibitor, or mixtures thereof.

38. The dual curable composition of claim 31, wherein the moiety A comprises at least one of an ester, an amide, a urethane, a urea, an acrylic oligomer, a urethane oligomer, a polyester oligomer, or mixtures thereof.

39. The dual curable composition of claim 38, wherein the moiety A comprises at least one of an ester, an amide, a urethane, a urea, or mixtures thereof.

40. The dual curable composition of claim 38, wherein the moiety A comprises at least one of an acrylic oligomer, a urethane oligomer, a polyester oligomer, or mixtures thereof.

41. The dual curable composition of claim 40, wherein the moiety A comprises a urethane oligomer.

42. The dual curable composition of claim 40, wherein the moiety A comprises a polyester oligomer.

43. A coating, sealant, adhesive, or composite resin comprising the dual curable composition of claim 31.

44. A corrosion-resistant coating, sealant, adhesive, or composite resin comprising the dual curable composition of claim 31.

45. A solvent-free, isocyanate-free, chromium-free coating, sealant, adhesive, or composite resin comprising the dual curable composition of claim 31.

46. A two part coating, sealant, adhesive, or composite resin comprising Part A and Part B;
Part A comprising:
the dual curable composition of claim 31; and
Part B comprising at least one of:

a corrosion inhibitor,
an organic acid functional component,
or mixtures thereof.

47. The two part coating, sealant, adhesive, or composite resin of claim 46;
Part A further comprising at least one of:
a photoinitiator, reactive monomer, defoamer, dispersant, pigment, stabilizer, or mixtures thereof; and
Part B further comprising at least one of:
a dispersant, reactive monomer, defoamer, oligomer, adhesion promoter, surfactant, flow agent, or mixtures thereof.

48. A method of preparing the composition of claim 31, the method comprising:
reacting an acrylated component comprising at least two acrylate groups with an aminosilane to form a reaction product comprising at least one acrylate group and at least one silane group;
reacting an epoxysilane with the reaction product comprising at least one acrylate group and at least one silane group to form a second reaction product comprising at least one acrylate group and at least two silane groups;
contacting the photoinitiator with the second reaction product comprising at least one acrylate group and at least two silane groups; and
optionally further comprising contacting an additional component of a curable composition with the second reaction product comprising at least one acrylate group and at least two silane groups.

49. The method according to claim 48, wherein the acrylated component comprises at least one of a diacrylate monomer, aliphatic polyether urethane diacrylate, aliphatic polyester urethane diacrylate, aromatic polyether urethane diacrylate, aromatic polyester urethane diacrylate, polyester diacrylate, polyether diacrylate, epoxy diacrylate, acrylated acrylic diacrylate, polyacrylate monomer, aliphatic polyether urethane polyacrylate, aliphatic polyester urethane polyacrylate, aromatic polyether urethane polyacrylate, aromatic polyester urethane polyacrylate, polyester polyacrylate, polyether polyacrylate, epoxy polyacrylate, acrylated acrylic polyacrylate, acrylate grafted polymer, acrylated polyolefin, acrylated polytetrafluoroethylene, acrylated polyester, acrylated polyamide, or mixtures thereof.

50. The method according to claim 48, wherein the aminosilane comprises at least one of 3-aminopropyltrimethoxysilane, 3-aminopropyltriethoxysilane, N-beta-(aminoethyl)-3-aminopropyltrimethoxysilane, N-beta-(aminoethyl)-3-aminopropyl methyldimethoxysilane, N-beta-(aminoethyl)-3-aminopropyltriethoxysilane, delta-aminoneohexyltrimethoxysilane, delta-aminoneohexylmethyldimethoxysilane, delta-aminoneohexyl triethoxysilane, or mixtures thereof.

51. The method according to claim 48, wherein the epoxysilane comprises at least one of 3-glycidoxypropyltrimethoxysilane, 3-glycidoxypropyltriethoxysilane, 3-glycidoxypropyl methyldimethoxysilane, 3-glycidoxypropylmethyldiethoxysilane, beta-(3,4-epoxycyclohexyl)ethyltrimethoxysilane, beta-(3,4-epoxycyclohexyl)ethyl triethoxysilane, or mixtures thereof.

52. The method of claim 48, wherein the additional component of a curable composition comprises at least one of a silane, an acrylate, a reactive monomer, an oligomer, cationic photoinitiator, dispersant, pigment, filler, flow agent, leveling agent, wetting agent, surfactant, defoamer, rheology modifier, stabilizer, antioxidant, adhesion promoter, corrosion inhibitor, or mixtures thereof.

53. A method of coating a substrate comprising applying to the substrate the dual curable composition of claim 31, and optionally exposing the coated substrate to a radiation source to cure the coating composition, wherein the radiation source is at least one of ultraviolet radiation or electron beam radiation.

54. The method of claim 53, wherein the substrate is selected from the group consisting of metal, concrete, stone, vinyl, wood, tile, ceramic, glass, plastic, paper, cardboard, asphalt, thermoplastic materials, thermoset materials, rubber, and composite materials.

55. The method of claim 53, wherein the substrate comprises a metal.

56. The method of claim 55, wherein the metal comprises aluminum, aluminum alloy, steel, stainless steel, magnesium alloy, or titanium.

57. The method of claim 53, wherein the substrate comprises an industrial or aerospace substrate.

58. A method of coating a substrate with the two part coating of claim 46, comprising:
a) Providing Part A and Part B;
b) Mixing Part A and Part B to form a mixture;
c) Applying the mixture to the substrate; and optionally
d) Exposing the coated substrate to a radiation source to cure the mixture.

59. A method of coating a substrate with the two part coating of claim 47, comprising:
a) Providing Part A and Part B;
b) Mixing Part A and Part B to form a mixture;
c) Applying the mixture to the substrate; and optionally
d) Exposing the coated substrate to a radiation source to cure the mixture.

60. A dual curable composition, comprising a compound represented by formula (I):

$$(acrylate)_a\text{-}(A)\text{-}(silane)_b \tag{I}$$

in which a and b are identical or different and are each represented by an integer greater than or equal to 1; and wherein the dual curable composition is further represented by formula (IV) and/or formula (V):

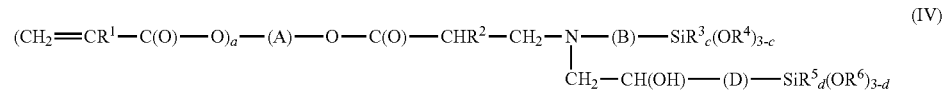

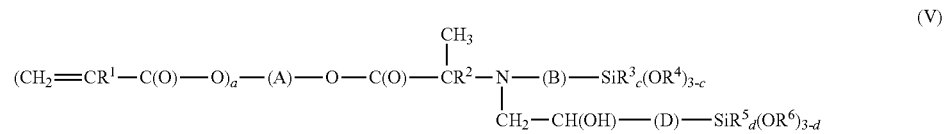

in which
a is represented by an integer greater than or equal to 1;
c is an integer equal to 0, 1, or 2;
d is an integer equal to 0, 1, or 2;
    the moiety A comprises an acrylic oligomer;
    the moiety B comprises at least one of an aliphatic hydrocarbon, a cycloaliphatic hydrocarbon, an aryl moiety, an ether, an amide, or mixtures thereof;
wherein the moiety B has a molecular weight less than or equal to 500;
    the moiety D comprises at least one of an aliphatic hydrocarbon, a cycloaliphatic hydrocarbon, an aryl moiety, an ether, or mixtures thereof;
wherein the moiety D has a molecular weight less than or equal to 500;
$R^1$ and $R^2$ are each independently H or an alkyl group having 1 to about 8 C atoms; and
$R^3$, $R^4$, $R^5$, and $R^6$ are each independently alkyl groups having 1 to about 8 C atoms;
wherein the dual curable composition has a molecular weight greater than or equal to 500; and
wherein the dual curable composition is radiation-curable and/or moisture curable.

61. The dual curable composition of claim 60, further comprising an additional component of a curable composition.

62. The dual curable composition of claim 60, further comprising a silane.

63. The dual curable composition of claim 60, further comprising a reactive monomer.

64. The dual curable composition of claim 60, further comprising an acrylate.

65. The dual curable composition of claim 60, further comprising an oligomer.

66. The dual curable composition of claim 60, further comprising a photoinitiator.

67. The dual curable composition of claim 60, further comprising a cationic photoinitiator.

68. The dual curable composition of claim 60, further comprising at least one of a dispersant, pigment, filler, flow agent, leveling agent, wetting agent, surfactant, defoamer, rheology modifier, stabilizer, antioxidant, adhesion promoter, corrosion inhibitor, or mixtures thereof.

69. The dual curable composition of claim 60, wherein the moiety A comprises the acrylic oligomer in mixture with at least one of an aliphatic hydrocarbon, a cycloaliphatic hydrocarbon, an aryl moiety, an ether, an ester, an amide, a urethane, a urea, a hydroxyl group-containing organic moiety, an epoxy oligomer, a urethane oligomer, or a polyester oligomer.

70. A coating, sealant, adhesive, or composite resin comprising the dual curable composition of claim 60.

71. A corrosion-resistant coating, sealant, adhesive, or composite resin comprising the dual curable composition of claim 60.

72. A solvent-free, isocyanate-free, chromium-free coating, sealant, adhesive, or composite resin comprising the dual curable composition of claim 60.

73. A two part coating, sealant, adhesive, or composite resin comprising Part A and Part B;
    Part A comprising:
    the dual curable composition of claim 60; and
    Part B comprising at least one of:
        a corrosion inhibitor,
        an organic acid functional component,
        or mixtures thereof.

74. The two part coating, sealant, adhesive, or composite resin of claim 73;
    Part A further comprising at least one of:
        a photoinitiator, reactive monomer, defoamer, dispersant, pigment, stabilizer, or mixtures thereof; and
    Part B further comprising at least one of:
        a dispersant, reactive monomer, defoamer, oligomer, adhesion promoter, surfactant, flow agent, or mixtures thereof.

75. A method of preparing the composition of claim 60, the method comprising:
    reacting the acrylic oligomer comprising at least two acrylate groups with an aminosilane to form a reaction product comprising at least one acrylate group and at least one silane group;
    reacting an epoxysilane with the reaction product comprising at least one acrylate group and at least one silane group to form a second reaction product comprising at least one acrylate group and at least two silane groups;
    optionally further comprising contacting an additional component of a curable composition with the second reaction product comprising at least one acrylate group and at least two silane groups.

76. The method according to claim 75, wherein the aminosilane comprises at least one of 3-aminopropyltrimethoxysilane, 3-aminopropyltriethoxysilane, N-beta-(aminoethyl)-3-aminopropyltrimethoxysilane, N-beta-(aminoethyl)-3-aminopropyl methyldimethoxysilane, N-beta-(aminoethyl)-3-aminopropyltriethoxysilane, delta-aminoneohexyltrimethoxysilane, delta-aminoneohexylmethyldimethoxysilane, delta-aminoneohexyl triethoxysilane, or mixtures thereof.

77. The method according to claim 75, wherein the epoxysilane comprises at least one of 3-glycidoxypropyltrimethoxysilane, 3-glycidoxypropyltriethoxysilane, 3-glycidoxypropyl methyldimethoxysilane, 3-glycidoxypropylmethyldiethoxysilane, beta-(3,4-epoxycyclohexyl)ethyltrimethoxysilane, beta-(3,4-epoxycyclohexyl)ethyl triethoxysilane, or mixtures thereof.

78. The method of claim 75, wherein the additional component of a curable composition comprises at least one of a silane, an acrylate, a reactive monomer, an oligomer, a photoinitiator, cationic photoinitiator, dispersant, pigment, filler, flow agent, leveling agent, wetting agent, surfactant, defoamer, rheology modifier, stabilizer, antioxidant, adhesion promoter, corrosion inhibitor, or mixtures thereof.

79. A method of coating a substrate comprising applying to the substrate the dual curable composition of claim 60, and optionally exposing the coated substrate to a radiation source to cure the coating composition, wherein the radiation source is at least one of ultraviolet radiation or electron beam radiation.

80. The method of claim 79, wherein the substrate is selected from the group consisting of metal, concrete, stone, vinyl, wood, tile, ceramic, glass, plastic, paper, cardboard, asphalt, thermoplastic materials, thermoset materials, rubber, and composite materials.

81. The method of claim 79, wherein the substrate comprises a metal.

82. The method of claim 81, wherein the metal comprises aluminum, aluminum alloy, steel, stainless steel, magnesium alloy, or titanium.

83. The method of claim 79, wherein the substrate comprises an industrial or aerospace substrate.

84. A method of coating a substrate with the two part coating of claim 73, comprising:
 a) Providing Part A and Part B;
 b) Mixing Part A and Part B to form a mixture;
 c) Applying the mixture to the substrate; and optionally
 d) Exposing the coated substrate to a radiation source to cure the mixture.

85. A method of coating a substrate with the two part coating of claim 74, comprising:
 a) Providing Part A and Part B;
 b) Mixing Part A and Part B to form a mixture;
 c) Applying the mixture to the substrate; and optionally
 d) Exposing the coated substrate to a radiation source to cure the mixture.

86. A method of coating a substrate comprising applying to the substrate the dual curable composition of claim 60, and allowing the coating composition to moisture cure in the absence of a radiation source.

87. A method of preparing the composition of claim 69, the method comprising:
 reacting the acrylic oligomer mixture, the acrylic oligomer comprising at least two acrylate groups with an aminosilane to form a reaction product comprising at least one acrylate group and at least one silane group;
 reacting an epoxysilane with the reaction product comprising at least one acrylate group and at least one silane group to form a second reaction product comprising at least one acrylate group and at least two silane groups;
 optionally further comprising contacting an additional component of a curable composition with the second reaction product comprising at least one acrylate group and at least two silane groups.

88. The method according to claim 87, wherein the acrylic oligomer mixture comprises at least one of a diacrylate monomer, aliphatic polyether urethane diacrylate, aliphatic polyester urethane diacrylate, aromatic polyether urethane diacrylate, aromatic polyester urethane diacrylate, polyester diacrylate, polyether diacrylate, epoxy diacrylate, acrylated acrylic diacrylate, polyacrylate monomer, aliphatic polyether urethane polyacrylate, aliphatic polyester urethane polyacrylate, aromatic polyether urethane polyacrylate, aromatic polyester urethane polyacrylate, polyester polyacrylate, polyether polyacrylate, epoxy polyacrylate, acrylated acrylic polyacrylate, acrylate grafted polymer, acrylated polyolefin, acrylated polytetrafluoroethylene, acrylated polyester, acrylated polyamide, or mixtures thereof.

89. The method according to claim 87, wherein the aminosilane comprises at least one of 3-aminopropyltrimethoxysilane, 3-aminopropyltriethoxysilane, N-beta-(aminoethyl)-3-aminopropyltrimethoxysilane, N-beta-(aminoethyl)-3-aminopropyl methyldimethoxysilane, N-beta-(aminoethyl)-3-aminopropyltriethoxysilane, delta-aminoneohexyltrimethoxysilane, delta-aminoneohexylmethyldimethoxysilane, delta-aminoneohexyl triethoxysilane, or mixtures thereof.

90. The method according to claim 87, wherein the epoxysilane comprises at least one of 3-glycidoxypropyltrimethoxysilane, 3-glycidoxypropyltriethoxysilane, 3-glycidoxypropyl methyldimethoxysilane, 3-glycidoxypropylmethyldiethoxysilane, beta-(3,4-epoxycyclohexyl)ethyltrimethoxysilane, beta-(3,4-epoxycyclohexyl)ethyl triethoxysilane, or mixtures thereof.

91. The method of claim 87, wherein the additional component of a curable composition comprises at least one of a silane, an acrylate, a reactive monomer, an oligomer, a photoinitiator, cationic photoinitiator, dispersant, pigment, filler, flow agent, leveling agent, wetting agent, surfactant, defoamer, rheology modifier, stabilizer, antioxidant, adhesion promoter, corrosion inhibitor, or mixtures thereof.

* * * * *